United States Patent
Mooneyham et al.

(10) Patent No.: US 12,403,226 B2
(45) Date of Patent: Sep. 2, 2025

(54) BREAST PUMP ACCESSORY SYSTEM

(71) Applicant: Momease Solutions, Inc., Plymouth, MN (US)

(72) Inventors: Ashley Mooneyham, Plymouth, MN (US); Loic Van Horne, Minneapolis, MN (US); Jared Hutar, Minneapolis, MN (US)

(73) Assignee: Momease Solutions, Inc., Plymouth, MN (US)

( * ) Notice: Subject to any disclaimer, the term of this patent is extended or adjusted under 35 U.S.C. 154(b) by 0 days.

(21) Appl. No.: 18/643,726

(22) Filed: Apr. 23, 2024

(65) Prior Publication Data

US 2024/0269355 A1 Aug. 15, 2024

Related U.S. Application Data

(63) Continuation-in-part of application No. 18/217,985, filed on Jul. 3, 2023.

(60) Provisional application No. 63/554,396, filed on Feb. 16, 2024, provisional application No. 63/358,069, filed on Jul. 1, 2022.

(51) Int. Cl.
*A61H 9/00* (2006.01)
*A41C 3/04* (2006.01)
*A61M 1/06* (2006.01)

(52) U.S. Cl.
CPC ......... *A61M 1/0697* (2021.05); *A61H 9/0078* (2013.01); *A61M 1/067* (2021.05); *A61H 2201/0207* (2013.01); *A61H 2205/082* (2013.01)

(58) Field of Classification Search
CPC ............ A61M 1/0697; A61M 2205/36; A61M 2205/366; A61H 9/0078; A61H 2205/082; A41C 3/04; A41C 3/105
See application file for complete search history.

(56) References Cited

U.S. PATENT DOCUMENTS 2,764,759 A * 10/1956 Gazelle .................. A41C 3/105
  450/38
5,616,125 A *  4/1997 Jelks ..................... A61M 1/062
  604/74

(Continued)

OTHER PUBLICATIONS

English translation of Lee (KR 10-1916817 B1) (Year: 2018).*

(Continued)

*Primary Examiner* — Justine R Yu
*Assistant Examiner* — Christopher E Miller
(74) *Attorney, Agent, or Firm* — Headland Law & Strategy; Matthew J. Smyth

(57) ABSTRACT

A pumping top may include a left panel and a right panel, each of the left panel and the right panel having a bottom edge and being configured to cover a side of a wearer's torso and cover and support a breast of the wearer. Each of the left panel and the right panel may include (i) an expandable bladder configured to contact and partially surround a corresponding breast of the wearer, (ii) a supply line coupled at one end to the bladder and at an opposite end to a connector disposed proximate the bottom edge, and (iii) a return line coupled at one end to the bladder and at an opposite end to the connector. The connector may be configured to couple to a circulating pump that is separate and distinct from the pumping top, which circulates warmed liquid through the pumping top.

17 Claims, 22 Drawing Sheets

(56) References Cited

U.S. PATENT DOCUMENTS

| | | | |
|---|---|---|---|
| 9,498,565 | B2 | 11/2016 | NoWroozi et al. |
| 10,046,097 | B2 | 8/2018 | Thompson et al. |
| D851,859 | S * | 6/2019 | Jackson .......................... D2/706 |
| 10,426,877 | B2 | 10/2019 | Sablotsky et al. |
| 10,507,131 | B2 * | 12/2019 | Parish ....................... A61F 7/02 |
| 10,758,653 | B2 | 9/2020 | Kumar et al. |
| 10,881,155 | B2 | 1/2021 | Hoth |
| 10,881,766 | B2 | 1/2021 | O'Toole et al. |
| 10,926,011 | B2 | 2/2021 | O'Toole et al. |
| 10,986,881 | B2 * | 4/2021 | Stanton ................ A41C 3/0064 |
| 11,260,151 | B2 | 3/2022 | O'Toole et al. |
| 11,311,654 | B2 | 4/2022 | O'Toole et al. |
| 11,324,866 | B2 | 5/2022 | O'Toole et al. |
| 11,357,893 | B2 | 6/2022 | O'Toole et al. |
| 11,357,894 | B2 | 6/2022 | O'Toole et al. |
| 11,376,352 | B2 | 7/2022 | O'Toole et al. |
| 11,395,593 | B2 * | 7/2022 | Kopelman ............ A61B 5/6804 |
| 11,413,380 | B2 | 8/2022 | O'Toole et al. |
| 11,583,468 | B2 | 2/2023 | Barkay |
| 11,666,689 | B2 | 6/2023 | Kumar et al. |
| 2001/0044593 | A1 * | 11/2001 | Lundy ....................... A41C 3/04 604/74 |
| 2002/0183719 | A1 * | 12/2002 | Morton ................ A61B 5/6834 604/74 |
| 2005/0234370 | A1 | 10/2005 | Beal et al. |
| 2006/0270973 | A1 * | 11/2006 | Chu ....................... A61M 1/067 604/74 |
| 2008/0000477 | A1 * | 1/2008 | Huster ..................... A61B 7/04 601/149 |
| 2010/0159801 | A1 * | 6/2010 | Abbaszadeh ......... A61M 1/062 450/86 |
| 2012/0197187 | A1 * | 8/2012 | LaFave ................. A61M 1/062 604/74 |
| 2012/0277636 | A1 * | 11/2012 | Blondheim ........... A61M 1/062 600/595 |
| 2014/0378946 | A1 | 12/2014 | Thompson et al. |
| 2015/0065994 | A1 * | 3/2015 | Fridman .............. A61M 1/0697 604/74 |
| 2015/0351956 | A1 | 12/2015 | Enderby |
| 2016/0213552 | A1 * | 7/2016 | Lindsay ................ A61B 5/6811 |
| 2017/0042256 | A1 * | 2/2017 | Kawasaki ............ A41C 3/0014 |
| 2017/0049164 | A1 | 2/2017 | Gruentzig |
| 2017/0112983 | A1 * | 4/2017 | Thorne ................. A61M 1/067 |
| 2017/0231291 | A1 * | 8/2017 | Lima ...................... A41C 3/105 450/38 |
| 2018/0326130 | A1 * | 11/2018 | Thompson .............. A61M 1/06 |
| 2019/0240109 | A1 | 8/2019 | Barkay |
| 2021/0145450 | A1 | 5/2021 | Gruentzig |
| 2021/0361473 | A1 | 11/2021 | Crowe |
| 2021/0361837 | A1 | 11/2021 | Bijoor |
| 2021/0401075 | A1 | 12/2021 | Gruentzig |
| 2023/0025217 | A1 | 1/2023 | Ford |

OTHER PUBLICATIONS

Amazon, Salmue Electric Breast Massage Bra Infrared Heating Vibration Chest Enlargement Stimulator Enhancer Massager Accelerate The Circulation Relieve Breasts, https://www.amazon.com/Vibration-Enlargement-Stimulator-Accelerate-Circulation/dp/B07PK3J3Y8; Accessed Jun. 2, 2023.

Amazon, IHHCOKX Longline Sports Bra Front Zip Crop Top for Women with Adjustable Straps Workout Top Cross Back Yoga Tank, https://www.amazon.com/IHHCOXK-Longline-Sports-Adjustable-Workout/dp/B098QPK38Q; accessed Jun. 2, 2023.

Sweat and Milk, Océane—Exclusive Hands Free Pumping Sports Bra (Noir), www.https://sweatandmilk.com/products/oceane-exclusively-handsfree-pumping-sports-bra-noir; accessed Jun. 2, 2023.

Temu, Women's Activewear: Solid Zipper Front Sports Bra—High Impact Push Up Yoga Tank Top—Wide Straps Running Fitness Cropped Top, https://www.temu.com/solid-zipper-front-sports-bra-high-impact-push-up-yoga-tank-top-wide-straps-running-fitness-cropped-top-womens-activewear-g-601099514049629.html; accessed Jun. 2, 2023.

The Breastfeeding Shop, Lilu Massage Bra, https://thebreastfeedingshop.com/product/lilu-massage-bra/ accessed Jun. 2, 2023.

* cited by examiner

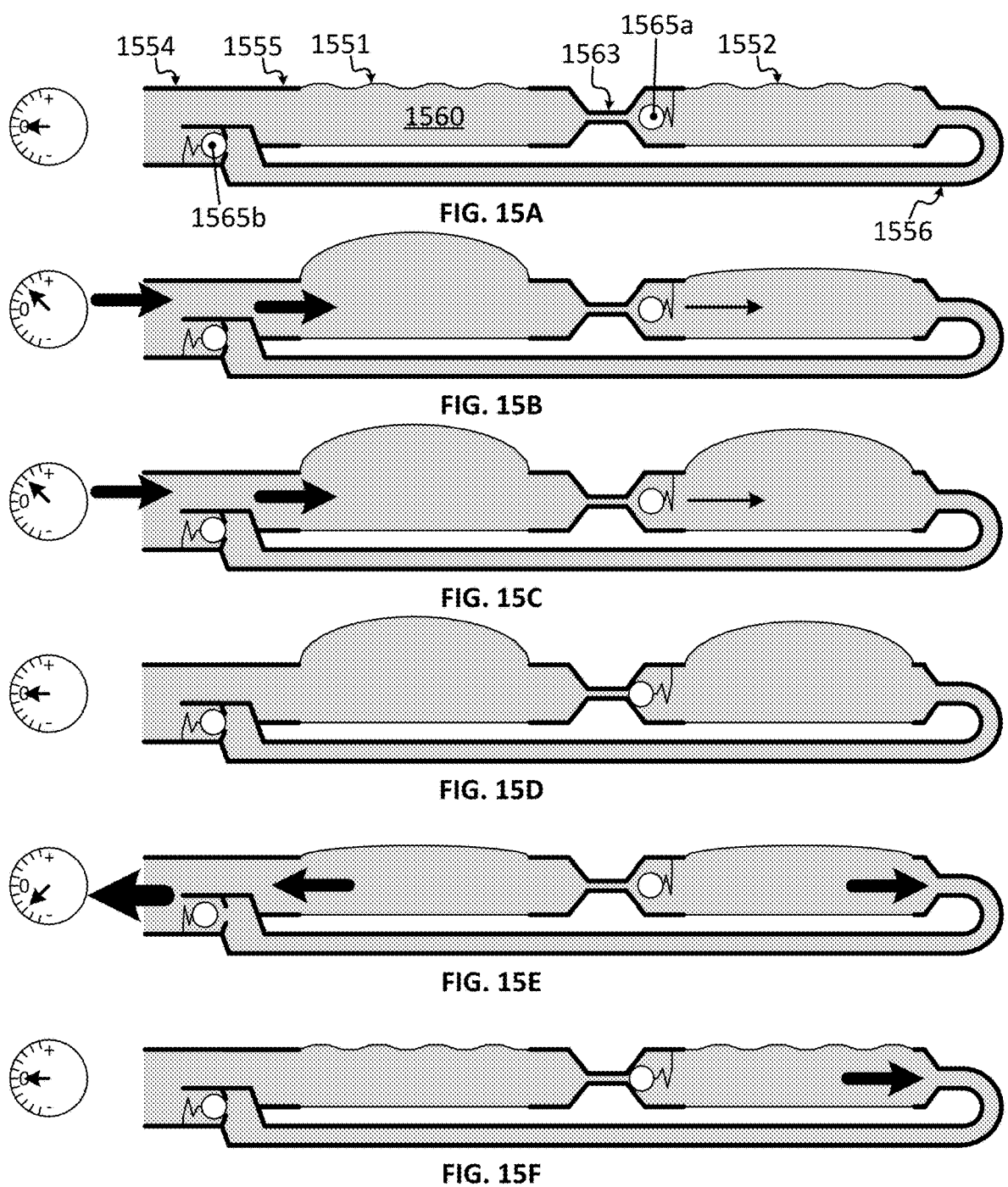

BREAST PUMP ACCESSORY SYSTEM

CROSS-REFERENCE TO RELATED APPLICATIONS

This application is a continuation-in-part of U.S. patent application Ser. No. 18/217,985, titled "Breast Pump Accessory System," filed on Jul. 3, 2023, which claims the benefit of U.S. Provisional Application Ser. No. 63/358,069, titled "Breast Pump Accessory System and Methods of Use," filed on Jul. 1, 2022. This application further claims the benefit of U.S. Provisional Application Ser. No. 63/554,396, titled "Breast Pump Accessory System," filed on Feb. 16, 2024.

This application incorporates the entire contents of the foregoing applications herein by reference.

TECHNICAL FIELD

Various implementations relate generally to accessory systems for use with breast pumps.

BACKGROUND

Traditional electric breast pumps that only use suction power to remove milk from a breast may only remove milk closest to the nipple of a breast-which may lead to incomplete extraction and low milk yield, sometimes despite long, uncomfortable pumping sessions. In contrast to such electric breast pumps, a nursing infant uses a combination of suction, warmth (e.g., from its mouth and hands), and movement (e.g., from its jaw and hands against the breast) to efficiently remove milk from the breast.

SUMMARY

A pumping top may include a left panel and a right panel, each of the left panel and the right panel having a bottom edge and being configured to cover a side of the wearer's torso and cover and support a breast of a wearer. The pumping top may further include a zipper configured to removably couple the left front panel and the right front panel. Each of the left panel and the right panel may include (i) an expandable bladder configured to contact and partially surround a corresponding breast of the wearer, (ii) a supply line coupled at one end to the bladder and at an opposite end to a connector disposed proximate the bottom edge, and (iii) a return line coupled at one end to the bladder and at an opposite end to the connector. The supply line and the return line may be disposed in the corresponding left or right panel. Each of the left panel and the right panel may have an aperture configured to receive an external breast pump that is separate and distinct from the pumping top. The connector may be configured to couple to a circulating pump that is separate and distinct from the pumping top, which circulating pump circulates warmed liquid to each supply line and receives return liquid from each return line.

In some implementations, each of the right and left panels comprise inner and outer layers, and the supply and return lines are disposed therebetween. Each connector may further include a valve to seal off the supply line and the return line when they are not coupled to the circulating pump. The cross-sectional shapes of the inlet line and the outlet line may be flat, with a width dimension being greater than a height dimension. The inlet and outlet lines may be configured to be disposed along the side of the wearer.

In some implementations, the expandable bladder of each side comprises a first expandable bladder and a second expandable bladder. The first expandable bladder may be coupled to the supply line, the second expandable bladder may be coupled to the return line, and the first expandable bladder may be coupled to the second expandable bladder with a tube. The first expandable bladder and the second expandable bladder may be expandable, and the tube may be non-expandable. The tube may have a reduced diameter relative to the first expandable bladder and the second expandable bladder, such that fluid flow from the first expandable bladder to the second expandable bladder is slowed to cause the first expandable bladder to fill prior to the filling of the second expandable bladder.

BRIEF DESCRIPTION OF THE DRAWINGS

FIGS. 15A-15F depict operation of another exemplary system having first and second bladders with a flow restrictor therebetween and two check valves in different positions.

DETAILED DESCRIPTION

Figure 1:
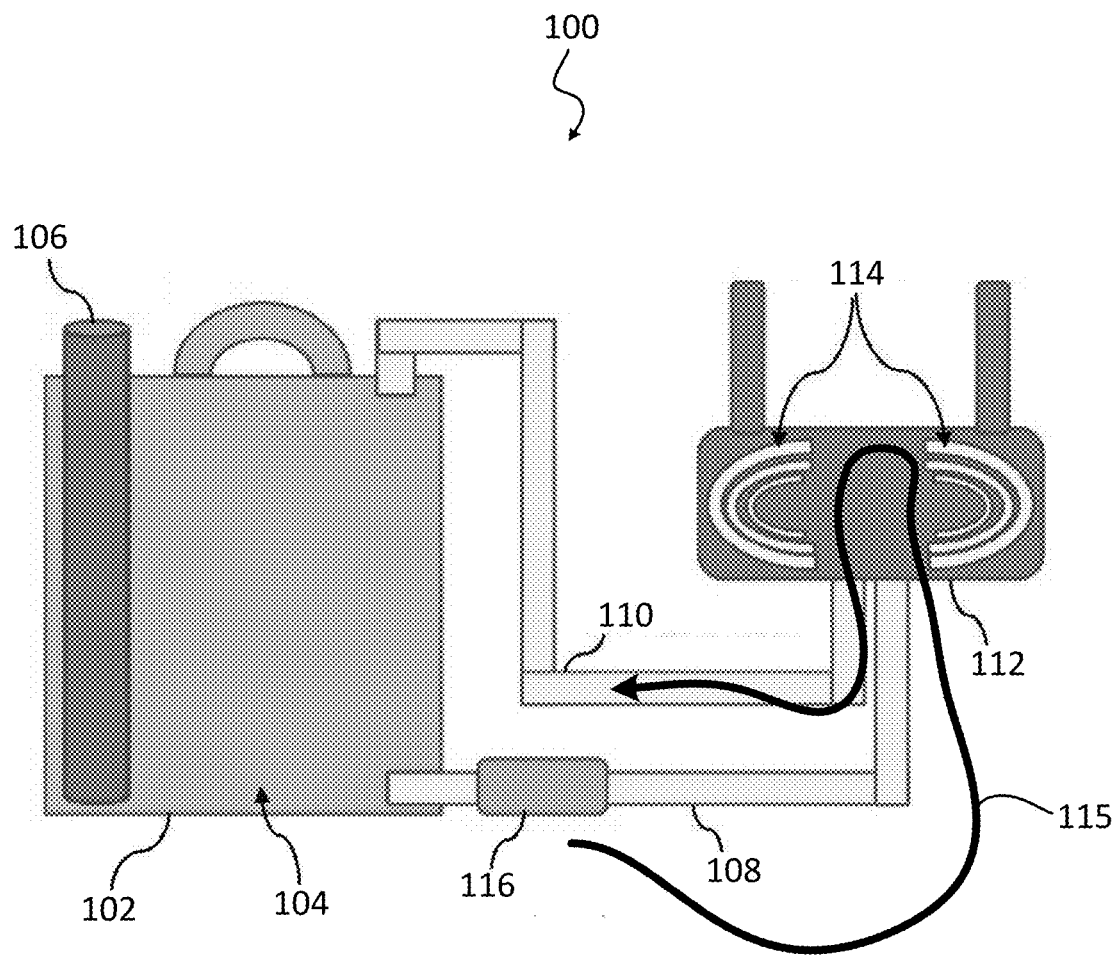
FIG. 1 illustrates a breast pump accessory system, according to some implementations.

FIG. 1 illustrates a breast pump accessory system 100. In some implementations, as shown in FIG. 1, the system 100 includes a fluid reservoir 102 configured to store fluid 104, a heating element 106 coupled to the fluid reservoir 102, and configured to heat the fluid 104, an inlet line 108, and an outlet line 110. A pump 116 is configured to transfer fluid 104 to a brassiere 112 via an inlet line 108 and receive fluid 104 back from the brassiere 112 via an outlet line 110.

In some implementations, the brassiere 112 comprises a plurality of expandable elements 114 that are in fluid communication with the inlet line 108 and the outlet line 110. And the fluid 104 circulated by the pump 116 may be used to inflate and deflate the plurality of expandable elements 114 to provide positive pressure, or massage, to each breast of a user of the system 100. Further, warming the fluid 104 via the heating element 106 can provide heat therapy to each breast of the user. In some implementations, the combination of massage and heat may help facilitate breast milk expression, in combination with the use of an external breast pump (not shown).

In some implementations, the pump 116 comprises a flow control mechanism configured to regulate the amount of fluid 104 allowed to flow through the inlet line 108. The pump 116 may comprise a flow rate control mechanism configured to regulate the speed at which the fluid 104 is flowed through the inlet line 108, expandable elements 114 of the brassiere 112 and back through the outlet line 110 (collectively, the circulation system 115). Adjustments to the volume or speed of the fluid 104 flow through the circulation system 115 may implement variations in massaging force (i.e., positive pressure) and speed effectuated by inflation of the plurality of expandable elements 114.

Figure 2:
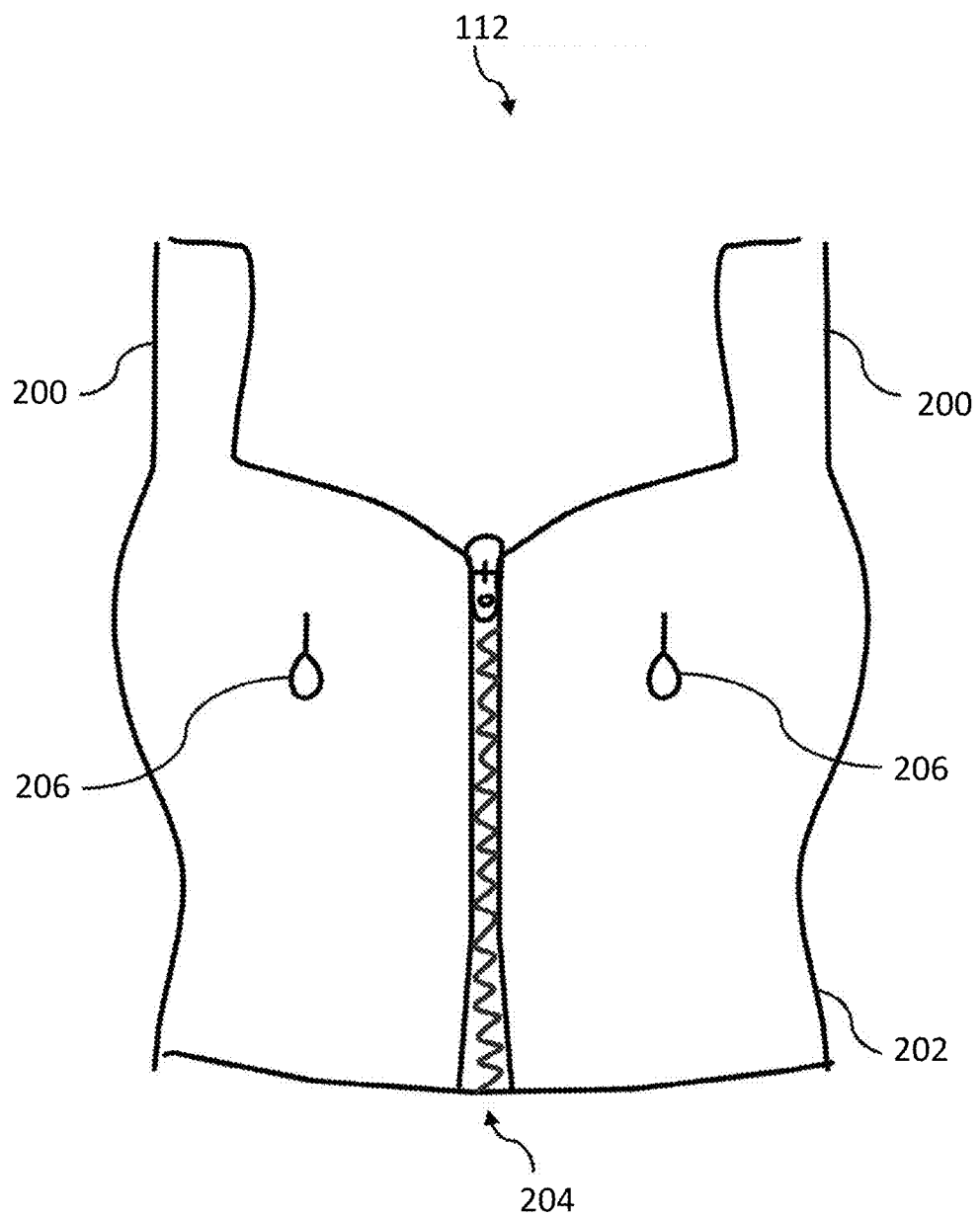
FIG. 2 illustrates a front view of a brassiere of the breast pump accessory system, according to some implementations.

FIG. 2 illustrates an exemplary front view of the brassiere 112. Similar to traditional "pumping bras," the brassiere 112 may include a plurality of holes 206, wherein each hole is configured to receive a breast pump flange—also commonly referred to as a nipple flange, nipple shield, or breast shield—to facilitate the use of a traditional breast pump. In some implementations (not shown), the system 100 includes a plurality of silicone nipple flanges, or breast shields, configured to be received by the plurality of holes 206 and couplable to an external breast pump (not shown). In such implementations, use of a soft and flexible material, such as silicone, rather than the traditional hard plastic, may enable the flanges/shields to sustain contact with the user's breasts during a pumping session involving suction and massage. For example, a flexible flange/shield may better move with the user's breast as the massaging pressure is applied than a rigid plastic flange/shield.

As shown, the brassiere 112 includes two straps 200 and a band 202, all of which may be a "wide fit" for added comfort for the user (e.g., as opposed to narrow straps and/or a narrow band, which may "dig in" to the user's shoulders and/or ribcage and may cause discomfort). As shown in FIG. 2, the brassiere 112 may also include a front closure via a zipper 204, which may improve the ease of use of the brassiere 112.

Figure 3:
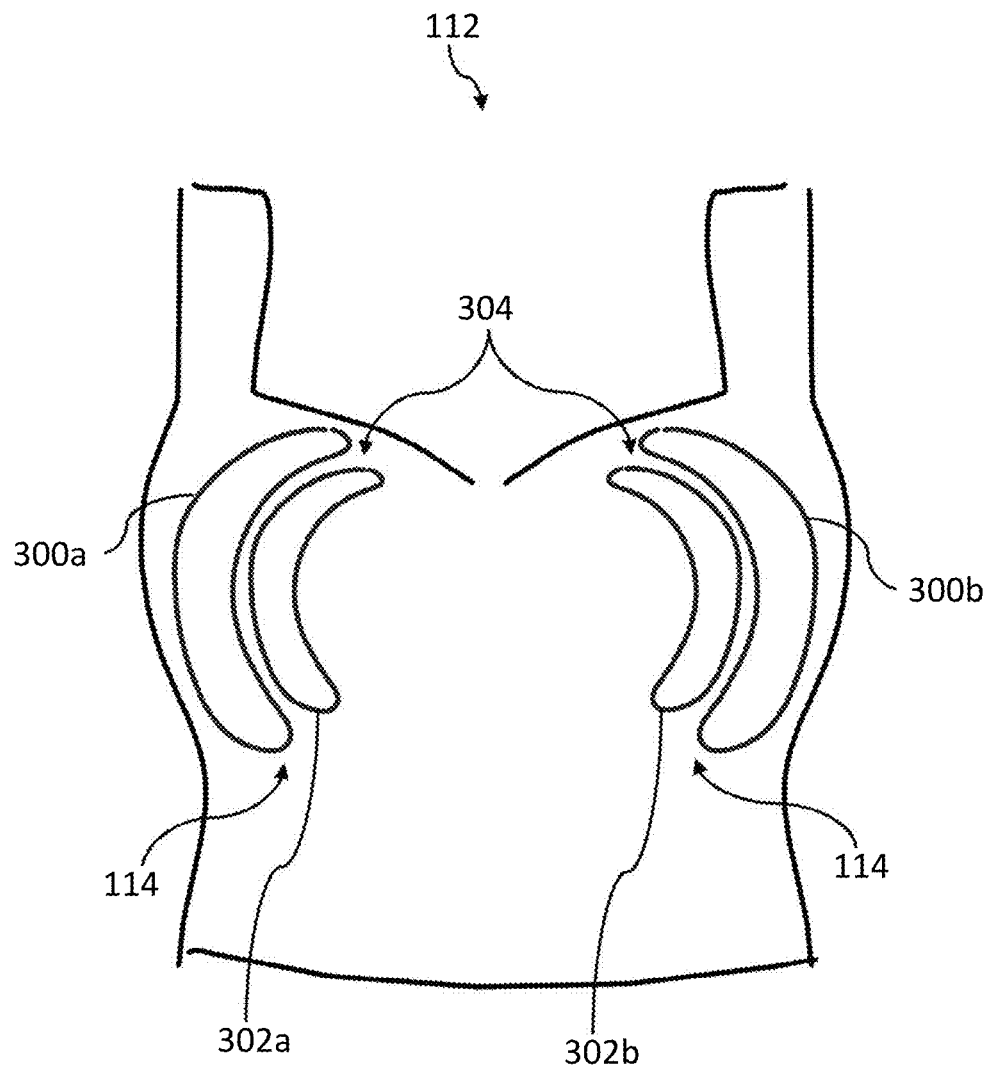
FIG. 3 illustrates the brassiere of the breast pump accessory system, including outer and inner expandable elements, according to some implementations.

FIG. 3 illustrates additional detail of exemplary expandable elements 114. As shown, the brassiere 112 includes a first outer expandable element 300a and a first inner expandable element 302a on one side, and a second outer expandable element 300b and a second inner expandable element 302b on the other side. Each of the first outer expandable element 300a, the second outer expandable element 300b, the first inner expandable element 302a, and the second inner expandable element 302b may define a C-shape 304, as illustrated. In some implementations, the C-shape 304 is sized and configured such that when the user is wearing the brassiere 112, the plurality of expandable elements 114 is configured to at least partially surround an outer portion of each breast of the user. In other implementations, the expandable elements 114 may be configured in another manner (e.g., in a horseshoe shape or inverted horseshoe shape).

In some implementations, the sizes of the expandable elements 114 may be configured to correspond to the size of the brassiere 112. For example, a smaller brassiere 112 may include smaller expandable elements 114 than those expandable elements 114 in a larger brassiere 112.

In some implementations, the expandable elements 114 may be differently sized relative to each other. For example, as shown in FIG. 3, the first and second outer expandable elements 300a, 300b are shown as larger than the first and second inner expandable elements 302a, 302b. In some implementations, this is a function of the their position relative to a user's breasts—the outer expandable elements 300a, 300b may be configured to contact the base of a user's breasts, whereas the inner expandable elements 302a, 302b may be configured to contact a smaller, more distal portion of the user's breasts; in some implementations, different sizes of the expandable elements 114 relative to each other can facilitate specific massage patterns (e.g., massage from the base of a user's breasts toward the nipples, to facilitate milk expression).

Different numbers of expandable elements 114 may be included in the brassiere 112. For example, two expandable elements on each side, 300a and 302a, and 300b and 302b, are shown in FIG. 3; whereas three expandable elements are depicted on each side in FIG. 1. In general, the plurality of expandable elements 114 may include one, two, three, four, or more than four expandable elements on each side of the brassiere 112.

Figure 4:
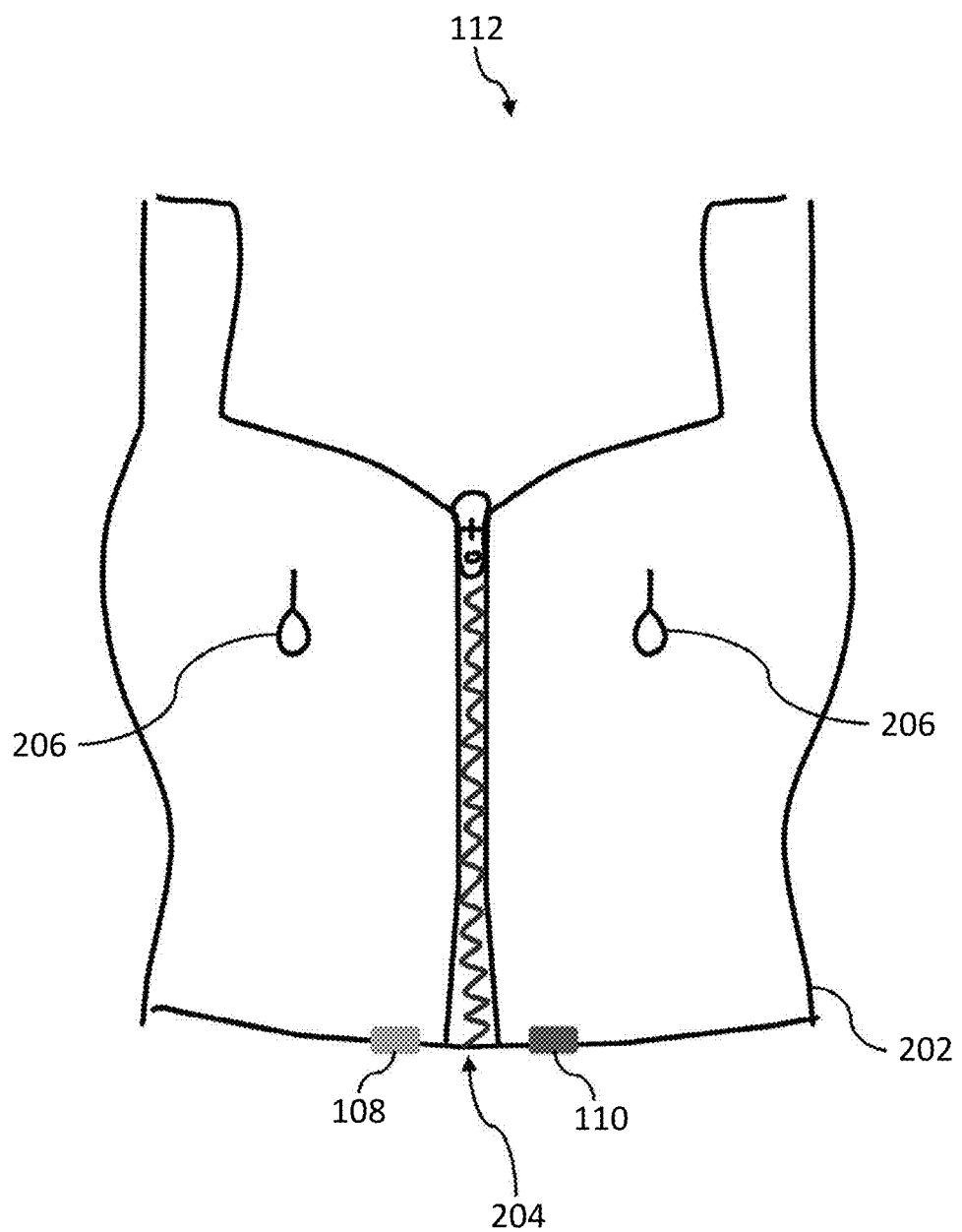
FIG. 4 illustrates a front view of the brassiere, including an inlet line and an outlet line, according to some implementations.

FIG. 4 provides another front view of the brassiere 112, showing an exemplary termination for the inlet line 108 and outlet line 110. As described above, fluid 104 may be circulated into inlet line 108, through the brassiere 112, and out of the outlet line 110. As shown in FIG. 4, inlet line 108 is shown as terminating on one side of the zipper 204, while the outlet line 110 is shown as terminating on the other side of the zipper 204. In other implementations, the inlet line 108 and the outlet line 110 may be located adjacent to one another and may be on the same size of the zipper 204. In other implementations, the inlet line 108 and outlet line 110 may be terminated in another location on the brassiere 112. In still other implementations, dedicated inlet and outlet lines may be provided to each side of the brassiere 112.

Figure 5A:
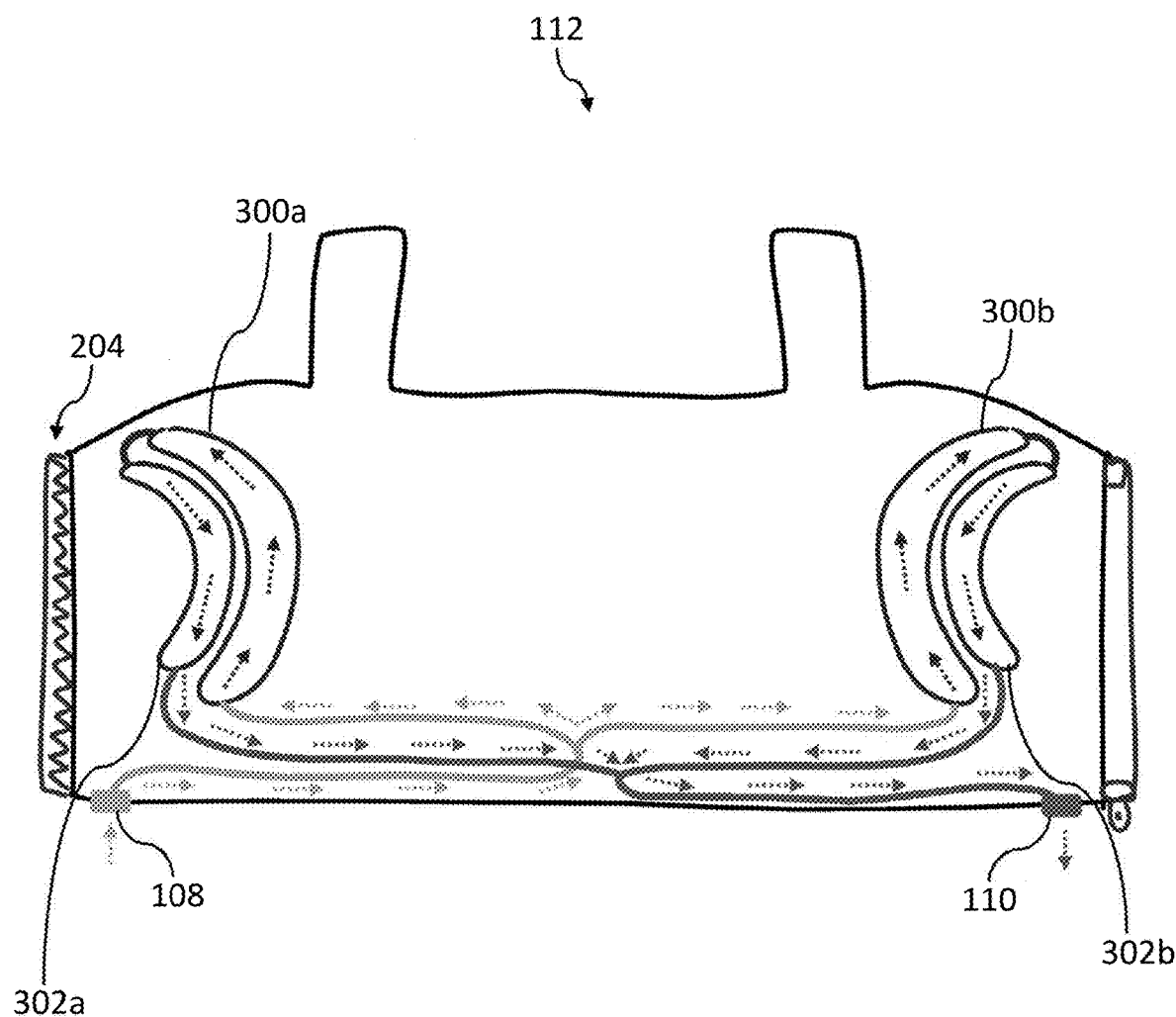
FIGS. 5A and 5B illustrate interior views of the brassiere, according to some implementations.

FIG. 5A illustrates an example flow path of the fluid 104 through the inlet line 108, each expandable element 114, and out the outlet line 110. The flow path shown in FIG. 5 is intended as a non-limiting example of how fluid 104 may flow through the brassiere 112. Other different flow paths are possible to achieve the desired outcome of applying massage and/or heat to a user's breast to improve the expression of breast milk.

As illustrated by the dashed arrows in the implementation shown in FIG. 5A, the fluid 104 enters the brassiere 112 via the inlet line 108. In some implementations, at least one of the inlet line 108 and the outlet line 110 are located between fabric layers of the brassiere 112. In some implementations, at least one of the inlet line 108 and the outlet line 110 may be located along an interior portion of the brassiere 112. In some implementations, at least one of the inlet line 108 and the outlet line 110 may be located along an exterior portion of the brassiere 112.

In some implementations, as shown, the inlet line 108 is configured to split into two lines, to transfer fluid 104 into the first outer expandable element 300a and the second outer expandable element 300b. After flowing up through the first and second outer expandable elements 300a, 300b, the fluid 104 may be configured to flow down through the first and second inner expandable elements 302a, 302b into separate segments of the outlet line 110. As illustrated in FIG. 5A, the segments of the outlet line 110 may converge into a single outlet line 110 to direct fluid 104 out of the brassiere 112. In some implementations, rather than a single line that splits off, the system 100 may include more than one inlet line 108 and/or more than one outlet line 110. For example, each of the first and second outer expandable elements 300a, 300b may be coupled to an independent inlet line 108. Similarly, each of the first and second inner expandable elements 302a, 302b may be coupled to an independent outlet line 110. In such implementations, the brassiere 112 may be coupled to four separate lines for transferring the fluid 104 between the fluid reservoir 102 and the brassiere 112.

Figure 5B:
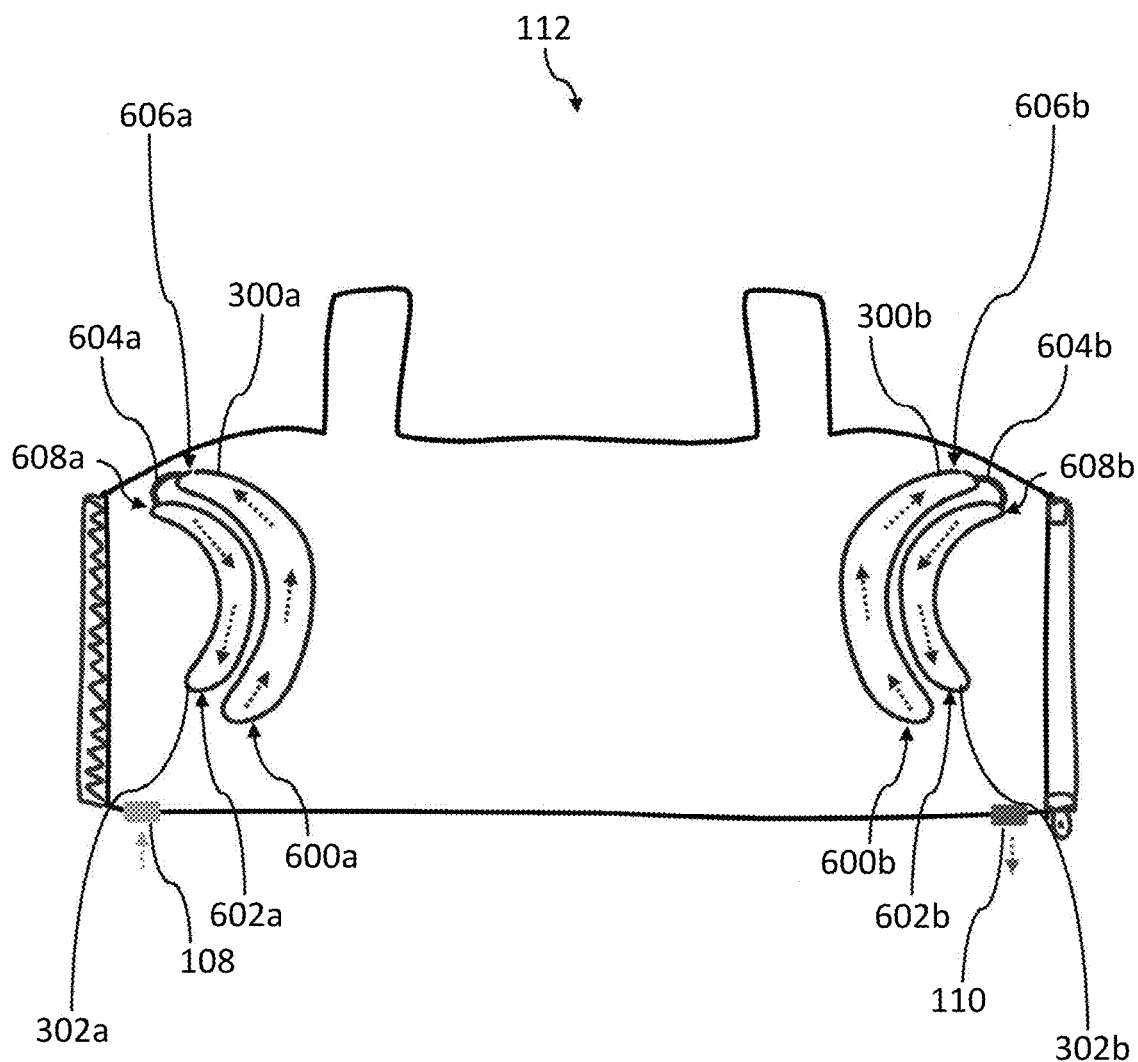

FIG. 5B provides additional detail for exemplary expandable elements 114, according to one implementation. In implementations in which the inlet line 108 splits into separate segments (e.g., as shown in FIG. 5A), one segment may couple to a bottom portion 600a of the first outer expandable element 300a and one may couple to a bottom portion 600b of the second outer expandable element 300b. Similarly, the outlet line 110 may comprise separate segments, one of which may couple to a bottom portion 602a of the first inner expandable element 302a and one of which may couple to a bottom portion 602b of the second inner expandable element 302b.

In some implementations, when fluid 104 moves up the first outer expandable element 300a from the bottom portion 600a to the top portion 606a, it reaches a first tube 604a, as shown in FIG. 5B. The first tube 604a may comprise a non-expandable material and be coupled to the top portion 606a of the first outer expandable element 300a and the top portion 608a of the first inner expandable element 302a, such that the fluid 104 transfer from first outer expandable element 300a to the first inner expandable element 302a, via the first tube 604. In some implementations, in addition to the first tube 604a being non-expandable (such that flow of fluid 104 through the first tube 604a does not cause any expansion, and thus does not effectuate pressure on the user at its location), the first tube 604a also has a reduced diameter relative to the expandable elements 300a and 302a. This reduced diameter can slow the transfer of the fluid 104 from the first outer expandable element 300a to the first inner expandable element 302a, to, in some implementations, facilitate an outer-to-inner massage force on a wearer's breast.

In some implementations, the pump 116 (see FIG. 1) may be configured to cause fluid 104 to flow through the system 100 substantially continuously while the system 100 is in use; in other implementations, the pump 116 may be configured to cause fluid 104 to intermittently flow through the system 100 (e.g., to implement a rhythmic massage function). A control system for the pump 116 may facilitate user adjustment of the frequency of intermittent flow, as well temperature, volume and/or flow of the fluid 104 (e.g., to vary the massage force and other parameters).

One flow path has been described, but other flow paths are possible by varying the orientation and shape of the outer expandable elements 300a and 300b, inner expandable elements 302a and 302b, first and second tubes 604a and 604b, and orientation of the inlet line(s) 108 and outlet line(s) 110. Thus, fluid 104 may flow down through the first and second outer expandable elements 300a, 300b, and up through the first and second inner expandable elements 302a, 302b; or it may flow in another manner.

In some implementations, the flow path of the fluid 104, as illustrated in FIGS. 5A and 5B through the C-shape 304 of the plurality of expandable elements 114, is configured to provide positive pressure to mimic massage patterns recommended by lactation consultants (e.g., a C-shape motion in an outward-in pattern, from the base of each breast toward the tip, or nipple). The filling of the first and second outer expandable elements 300a, 300b, followed by the filling of the first and second inner expandable elements 302a, 302b may be configured to provide massage of each breast in an outward-in pattern. Further, the plurality of expandable elements 114 may be configured to fill and empty in a sequential pattern. For example, the first and second outer expandable elements 300a, 300b may be configured to fill, then empty as the first and second inner expandable elements 302a, 302b fill with the fluid 104.

Figure 6:
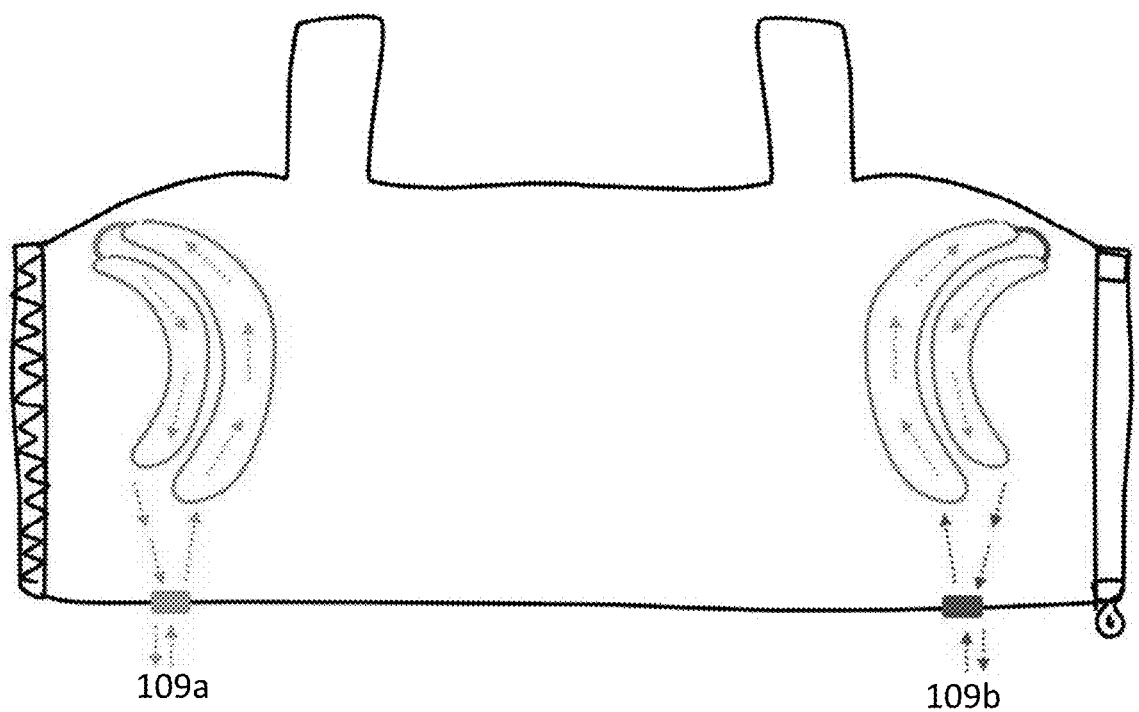
FIG. 6 illustrates an interior view of the brassiere, with another exemplary flow path.

Several flow patterns may be possible with the system 100. In some implementations, the first and second outer expandable elements 300a, 300b are configured to fill substantially simultaneously. Similarly, the first and second inner expandable elements 302a, 302b may be configured to fill substantially simultaneously. In some implementations, the first outer expandable element 300a is configured to at least partially fill before the second outer expandable element 300b (or vice-versa), and the first inner expandable element 302a is configured to at least partially fill before the second inner expandable element 302b (or vice-versa). In some implementations, the system 100 is configured such that the fluid 104 is configured to flow into only one side of the brassiere 112 at a time. In such implementations, a user may be able to nurse an infant from one breast while simultaneously pumping from the other breast. In other implementations (e.g., such as the one illustrated in FIG. 6—viewed from the back/inside), inlet/outlet ports 109a and 109b may be provided for each side of a pumping top.

Figure 7A:
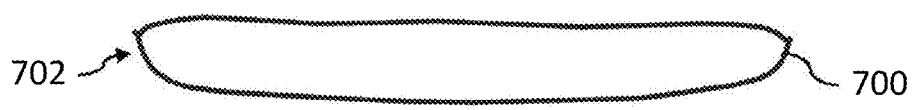
FIGS. 7A, 7B, and 7C illustrate an expandable element in varying stages of inflation, according to some implementations.
Figure 7B:
Figure 7C:

Referring now to FIGS. 7A, 7B, and 7C, an expandable element 700 is shown in varying states of inflation or expansion. As shown, the expandable element 700 can depict any of the expandable elements 114, including the first outer expandable element 300a, the first inner expandable element 302a, the second outer expandable element 300b, and the second inner expandable element 302b. In some implementations, the system 100 is configured such that a user (e.g., through a flow control mechanism) may adjust the amount of fluid 104 flowing through the plurality of expandable elements 114, thereby adjusting the volume and/or pressure (and thus massage intensity) applied to each breast. FIG. 7A illustrates an expandable element 700 in a deflated state 702, while FIG. 7C illustrates the expandable element 700 in a fully inflated state 706. FIG. 7B shows the expandable element 700 in a partially inflated state 704 and is intended to represent any level of "partial inflation" possible.

The system 100 may also facilitate user control of temperature. In some implementations, the heating element 106 includes an adjustment mechanism configured to enable users to adjust the temperature of the fluid 104 to suit their preference and/or needs. Users may find that different temperatures are desirable for different goals (e.g., relaxation, pain relief, or letdown promotion). In some implementations, the heating element 106 can be entirely turned off such that the fluid 104 is not heated before/after flowing through the system 100. This feature may be desirable, for example, when a user uses the system 100 on a hot day or inside a hot building. In some implementations, a cooling element is also provided to facilitate therapeutically cooling temperatures (e.g., to reduce swelling or pain). In other implementations, no cooling element may be provided, but the system 100 may be configured to allow a user to add ice or other cooling agents to circulating fluid. The temperature range of the fluid 104 may be configurable at least between 50 and 120 degrees Fahrenheit, but in some implementations, a greater range may be possible (e.g., below 50 degrees, to close to 32 degrees; or above 120 degrees, to 130 degrees or greater (e.g., to facilitate initial heating of the bladders and lines in the system, at which point, temperature may be reduced)).

A system 100 that enables adjustment of both the massage intensity and the temperature can facilitate a highly customizable pumping session. For example, a user can vary the massage intensity and temperature (and, separately, the suction force of an external breast pump) to find her optimal combination. Combining massage, heat, or both with suction may also reduce the need to "max out" the suction force in an effort to maximize breast milk expression, resulting in a more comfortable pumping experience for the user. Further, adding massage and/or heat to the suction force provided by a traditional breast pump may increase the speed of breast milk expression, resulting in shorter pumping sessions for the user.

Figure 8:
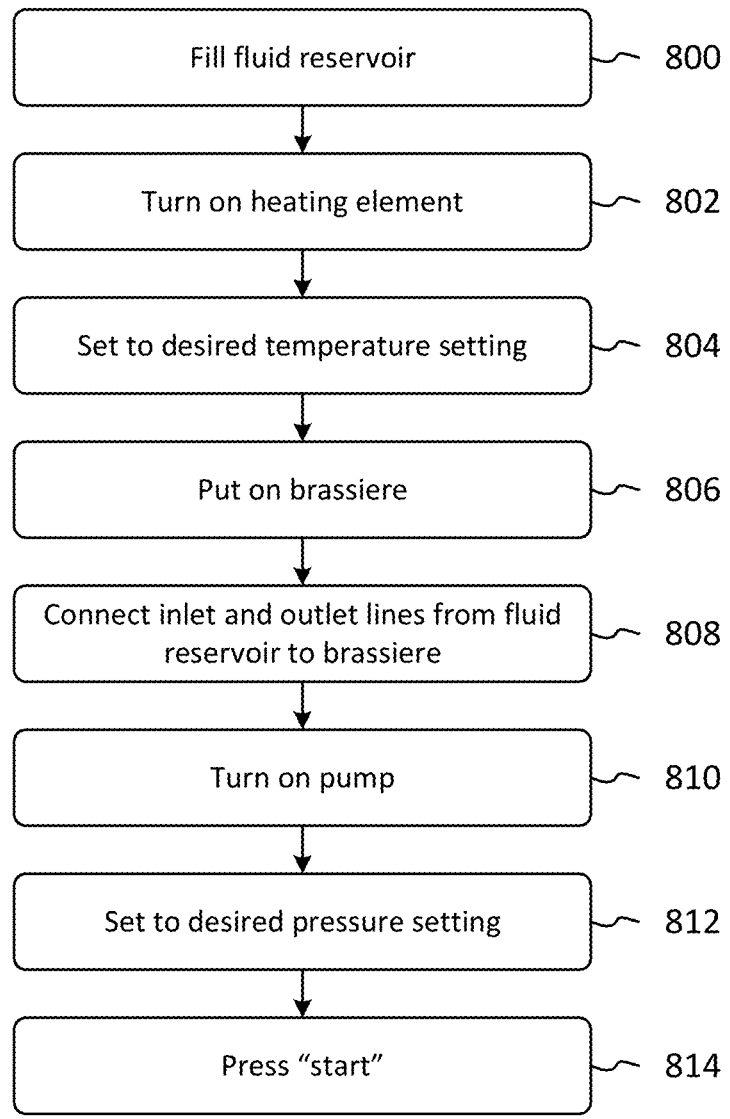
FIG. 8 illustrates a flowchart demonstrating the use of the breast pump accessory system, according to some implementations.

FIG. 8 illustrates an exemplary method for using the system 100. In some implementations, the method starts with a user filling (800) the fluid reservoir (e.g., reservoir 102, shown in FIG. 1). The fluid reservoir 102 may be sized and configured for portability (e.g., about the size of a tea kettle or smaller, in some implementations). The method includes turning on (802) the heating element 106. As previously discussed, the heating element 106 may include a temperature adjustment mechanism allowing the user to set (804) a desired temperature. If a user does not desire to heat the fluid 104, steps 802 and 804 may be skipped.

The method includes the user putting on (806) the brassiere 112. In some implementations, the brassiere 112 is configured for all-day wear; thus, the user may already have put on (806) the brassiere 112 prior to execution of the other steps.

The user may connect (808) the inlet line 108 and the outlet line 110 from the fluid reservoir 102 to the brassiere 112, and turn on (810) the pump 116 to prepare to initiate the flow of the fluid 104 through the inlet line 108. The pump 116 may include a flow control mechanism and/or a flow rate control mechanism, allowing the user to set (812) a desired pressure setting. In some implementations, the flow rate may include a range of at least 0 to 7 L/min. After all settings have been configured, the user may initiate flow by actuating (814) a control (e.g., a "start" control). The above-described method is merely exemplary. In other implementations, steps may be omitted or modified; other steps may be included.

The system 100 may include a control panel with various user controls including, but not limited to, a power button, a start/stop button, a time button, a pressure control button, a temperature control button, and any number of other user controls not specifically stated in this disclosure. The control panel may be fixedly coupled to an element of the system 100, for example, the circulating pump 934. In some implementations, the control panel is a remote device, physically disconnected from other portions of the system. For example, the system 100 may be configured to be controlled by a remote application on a remote computing device, such as a smartphone, tablet, or laptop. In some implementations, the system 100 is battery-powered (e.g., powered with direct current (DC)); in other implementations, the system 100 may run on alternating current (AC) power and require a connection to a power outlet for operation.

In some implementations, the expandable elements 114 are fixedly coupled to the brassiere 112 and are sufficiently durable to withstand laundering (e.g., hand or machine washing). Similarly, at least a portion of the inlet line 108 and the outlet line 110 (e.g., the portions illustrated in FIG. 5) may be fixedly coupled to the brassiere 112 and may also be sufficiently durable to withstand laundering. In some implementations, at least one of the plurality of expandable elements 114, the inlet line 108, and the outlet line 110 are removably coupled to the brassiere 112 and are configured to be removed prior to laundering the brassiere 112.

In some implementations, the plurality of expandable elements 114 may comprise individually expandable "pockets" at least partially separated by non-compliant portions. In such implementations, the fluid 104 may take a zig-zag pattern through each expandable element rather than the up and down pattern illustrated in FIGS. 5 and 6. Further, rather than fluid 104, the plurality of expandable elements 114 may be configured to fill with air. Any number of methods for providing pneumatic compression, positive pressure, or other massage elements may be employed by the system 100 to facilitate breast milk expression.

In some implementations, rather than pressure, the "massage" element of the system 100 may include vibration. For example, the brassiere 112 may be detachably or fixedly coupled to at least one vibrating element configured to provide sufficient movement to facilitate breast milk expression. Rather than heated fluid, the system 100 may include resistive circuits to apply heat to each breast of the user. For example, wires may be detachably or fixedly coupled to the brassiere 112 and configured to heat up in order to warm the brassiere 112. Other methods of applying heat may be suitable for use with the system 100.

Figure 9A:
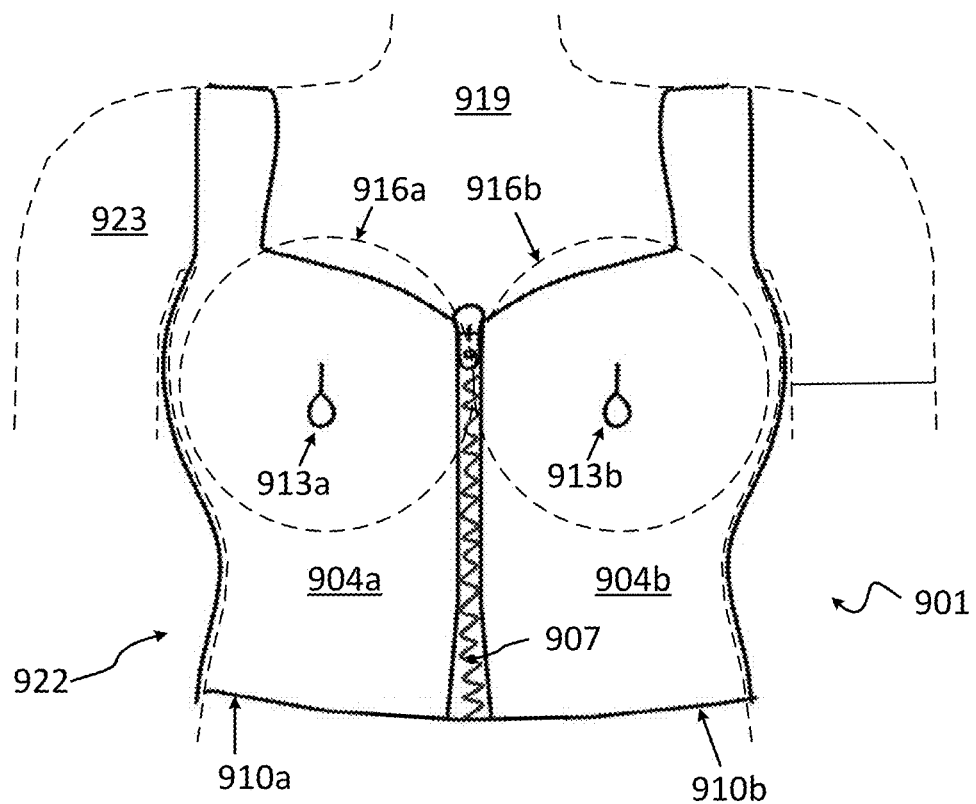
FIGS. 9A and 9B illustrate an exemplary pumping top that is configured to be worn by a nursing user to facilitate expression of breast milk.
Figure 9B:
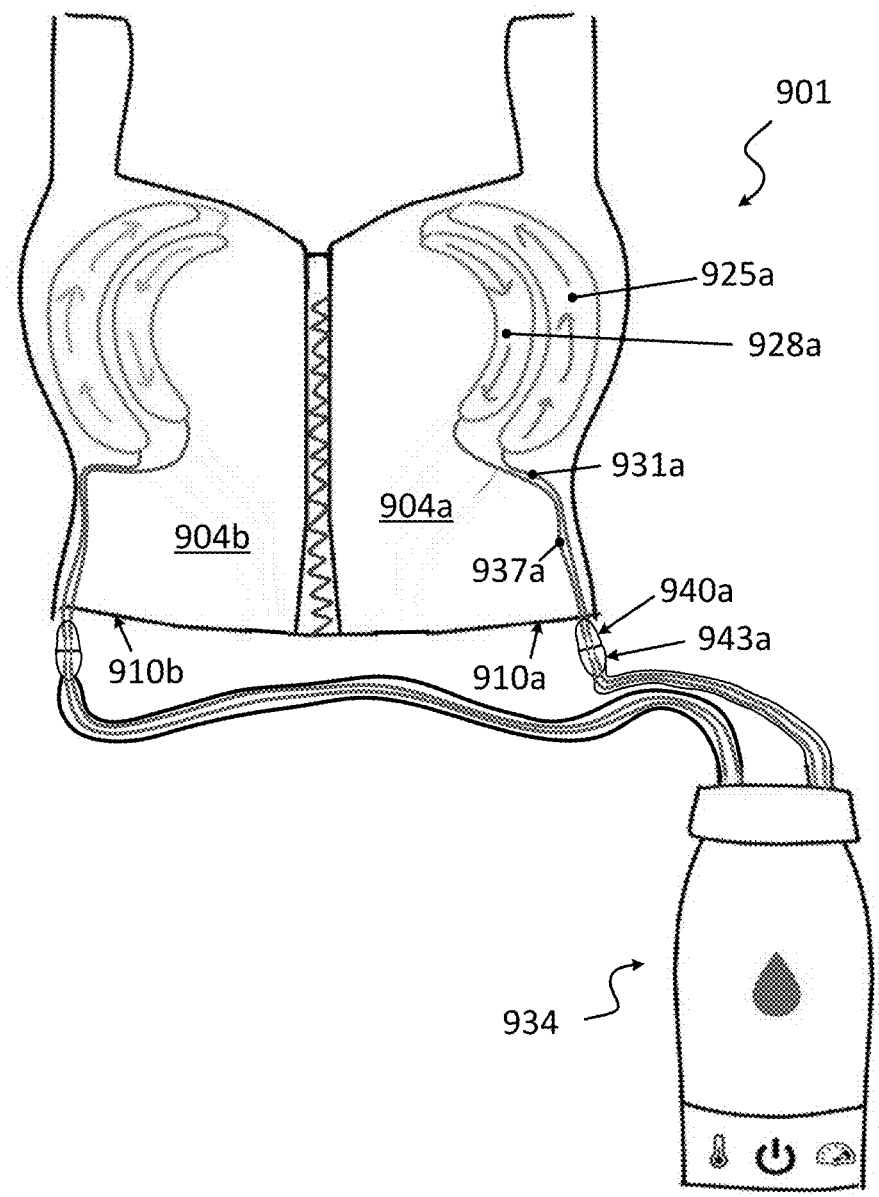

FIGS. 9A and 9B illustrate another implementation of an exemplary pumping top 901 that is configured to be worn by a nursing user to facilitate expression of breast milk (e.g., in the context of pumping). FIG. 9A illustrates an exterior front of the pumping top 901; and FIG. 9B illustrates an interior front of the pumping top 901. As shown, the pumping top 901 includes a right panel 904a and a left panel 904b (right and left from the perspective of a nursing user 919 wearing the pumping top 901).

As shown, a zipper 907 removably couples the right panel 904a and left panel 904b. Each of the right panel 904a and left panel 904b has a bottom edge, 910a and 910b, respectively; and in some implementations, the panels 904a and 904b are configured to extend some distance below the breasts 916a and 916b of the wearer 919 to form a tank-style or longline bra (e.g., for improved comfort). In such implementations, the pumping top 901 covers a side and front of the torso 922 of the wearer 919 and at least partially covers and supports each breast 916a or 916b of the wearer 919.

As shown, each of the right panel 904a and left panel 904b includes an aperture 913a or 913b that is configured to receive a breast flange associated with an external breast pump (not shown). In some implementations, each aperture 913a or 913b may comprise a circular opening that is configured to be aligned close to the corresponding nipple of the user 919, and a slot that extends away from, or on either side of, the circular opening to enable a breast flange to be manipulated through the pumping top 901.

As shown in FIG. 9B, each of the left panel 904b and right panel 904a includes an expandable bladder (as shown, an outer expandable bladder and inner expandable bladder are shown on each side, including right outer expandable bladder 925a and right inner expandable bladder 928a). In some implementations, as shown, the expandable bladders 925a and 928a are configured to contact (either directly or through a material layer of the pumping top 901) a corresponding breast of the wearer 919. A supply line 931a supplies the expandable bladder 925a with fluid that is circulated by a circulating pump 934, and a return line 934a routes fluid back to the circulating pump 934. (As used herein, a "circulating pump" may refer to both a pump that drives fluid through a loop having a dedicated supply line 931a and return line 934a, or to a pump that drives fluid in and out of a blind channel (e.g., as described below with reference to FIGS. 11A-13F); and "circulating" may refer to flow of fluid in either a loop or into and out of a channel.) In some implementations, as shown, a similar supply line, return line and one or more expandable bladders are provided with the other panel.

Figure 9C:
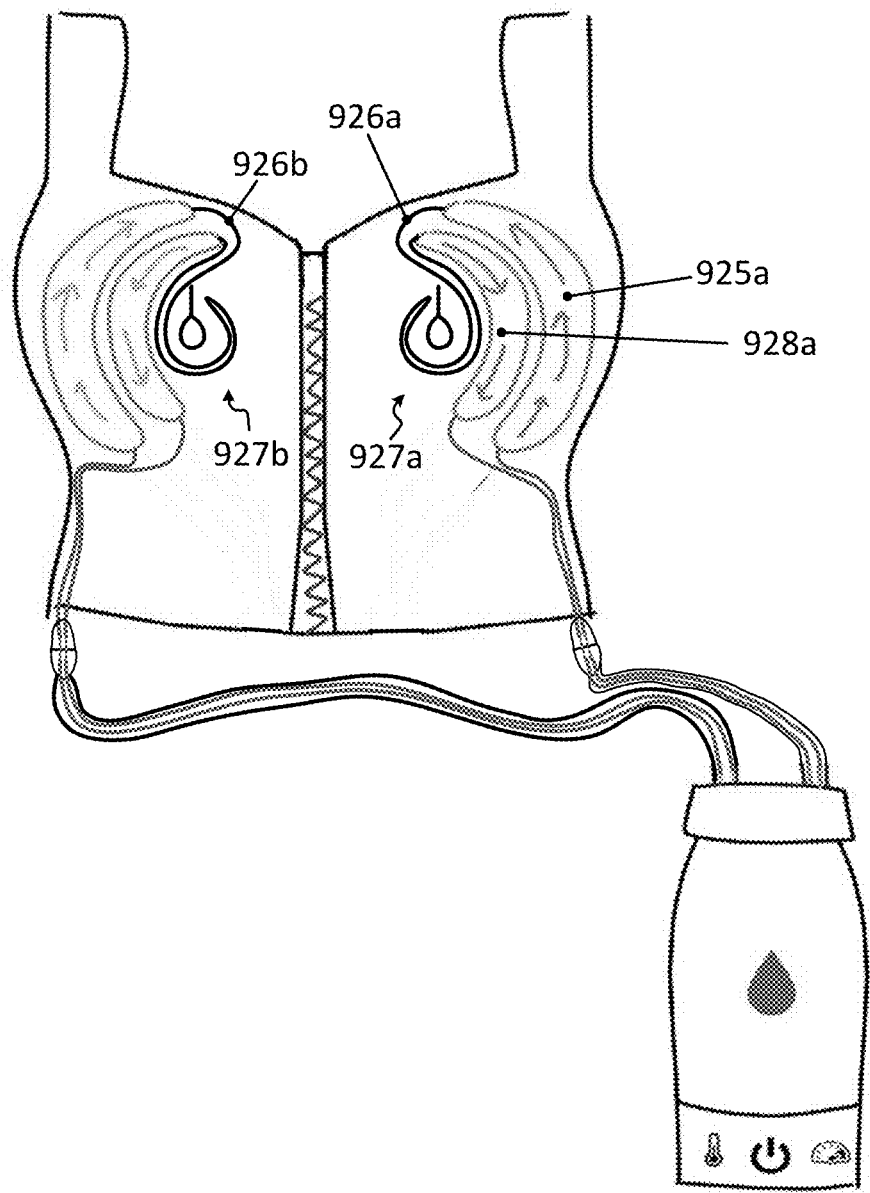
FIGS. 9C and 9D illustrate exemplary implementations that provide a warming function independently of a massage function.

FIG. 9C illustrates a variation of the implementation shown in FIG. 9B—specifically, an implementation in which dedicated warming loops 927a and 927b are provided. The warming loops may be non-expandable sections (that is, sections that do not expand and contract like the bladder sections) that may include segments 926a and 926b that couple the outer bladder (e.g., outer bladder 925a) to the inner bladder (e.g., inner bladder 928a). Such warming loops 927a and 927b may provide warming of a user's breasts, separate from the massage function provided by the bladders (e.g., bladders 925a and 928a). In some implementations, "warming loops" may provide cooling as well—that is, as used herein, "warming" may refer to a temperature regulation function that either warms or cools.

Figure 9D:
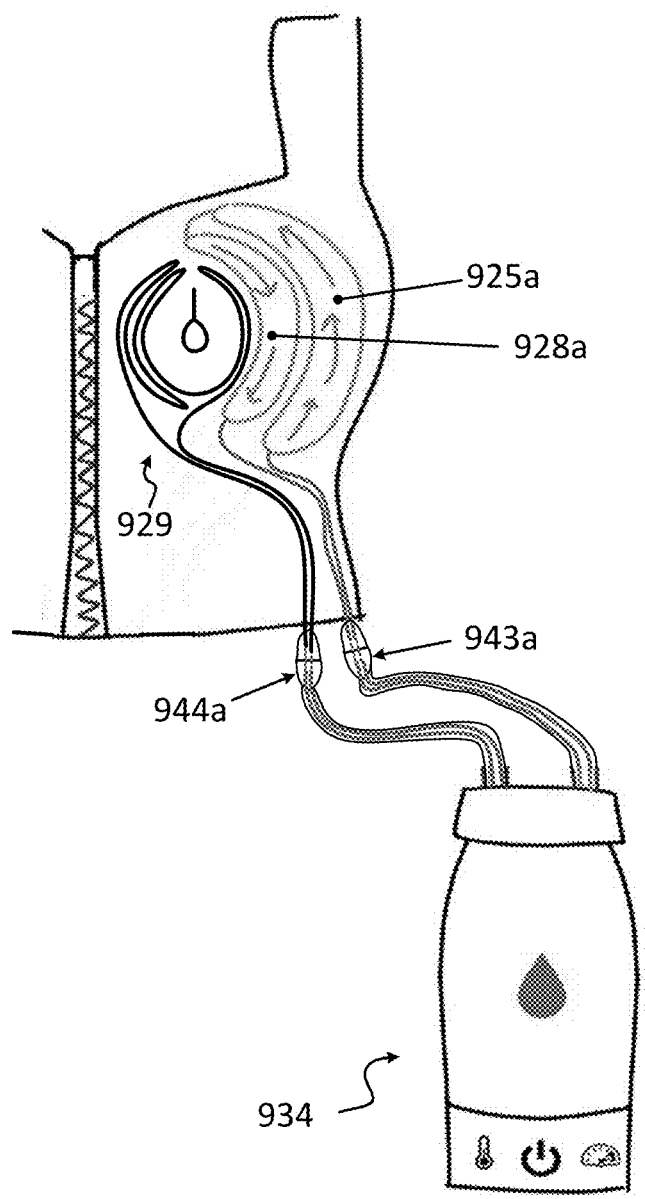

FIG. 9D illustrates another implementation in which a warming loop 929 is provided that is independent of the bladders 925a and 928a. In such an implementation, a warming function may be provided whether or not a massage function is also provided. As shown, one connector 943a may be provided for the bladders and massage function; another connector 944a may be provided for the warming function; and each function (e.g., massage and warming) may be separately controllable by the circulating pump 934.

In either implementation shown in FIGS. 9C and 9D, the warming function may be more expansive than may otherwise be possible when warming and massage functions are combined. That is, warming may be provided over a greater portion of the user's breasts (e.g., over substantially 360 degrees, at least adjacent the user's nipples, and especially around the breasts in areas other than those contacted by the bladders). Moreover, the warming function may be substantially continuously provided, regardless of the frequency of any massage function or of the point in a massage cycle the bladders may be at. By disposing the warming path 929 opposite the bladders, some implementations may advantageously warm a large area between the breasts. In addition, implementations that employ non-expandable channels may occupy less space than the bladders, facilitating more surface contact for warming than the bladders.

While FIGS. 9C and 9D illustrate implementations in which warming loops 927a or 929 comprise a "channel," or tubular construction, "patch" designs are also possible. For example, some implementations may include a thin, contoured reservoir (not shown) that can be filled with fluid and employed as a heating patch. Such a patch may be configured to provide access to the nipple via an aperture. That is, the reservoir may be segmented to enable a breast pump flange (not shown) to be disposed through such an aperture and be placed in contact with a user's nipple during a pumping operation.

In some implementations, a connector 940a may be provided at an end of the supply line 931a and return line 931b and may be configured to couple with a mating connector 943a that is coupled to supply and return lines of the circulating pump 934. In such implementations, the circulating pump 934 may be easily disconnected from the pumping top 901 and reconnected when desired. In some implementations, the connectors (e.g., connector 940a) may be disposed proximate a bottom edge (e.g., coinciding with or close to a natural boundary for other clothing that may be worn over the pumping top 901, such that the connector 943 may be both easily accessed and easily hidden when not in use).

Figures 9E, 9F:
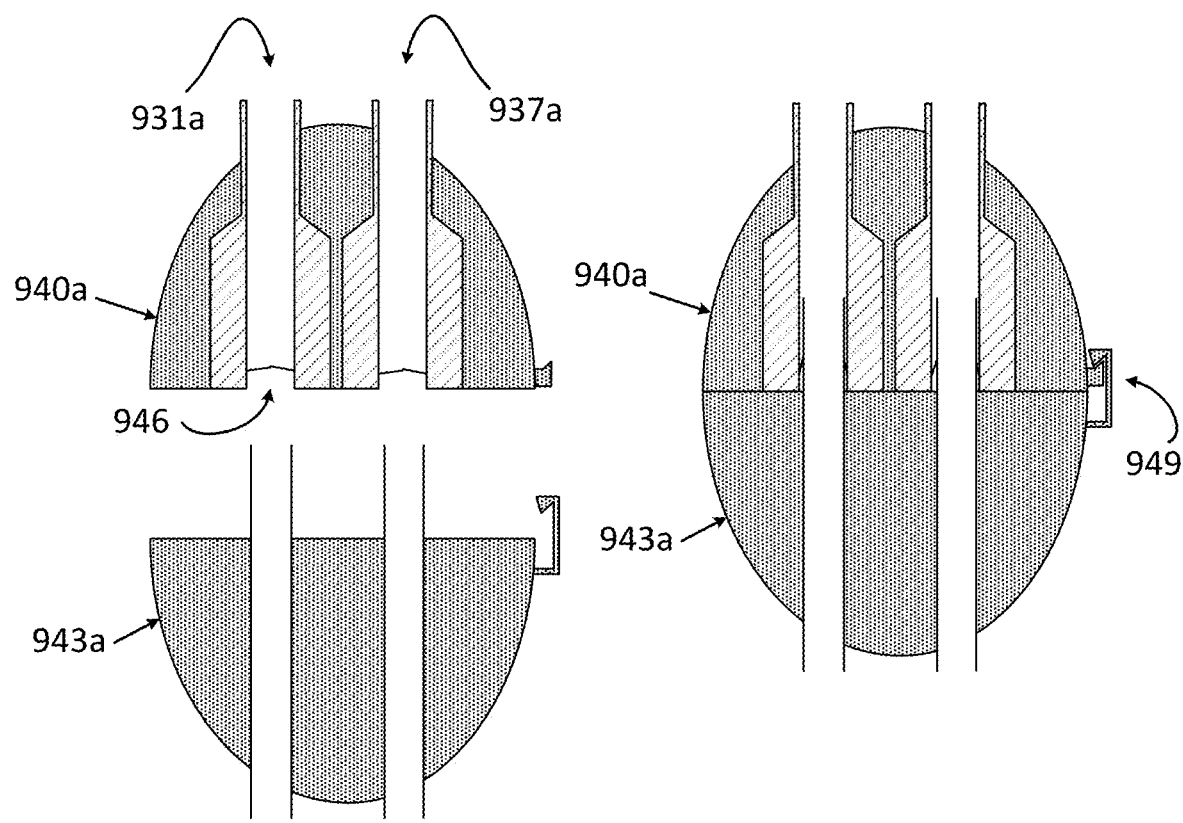
FIGS. 9E and 9F illustrate details of exemplary mating connectors to couple the pumping top to a circulating pump.

FIGS. 9E and 9F illustrate additional detail of exemplary mating connectors 940a and 943a. In FIG. 9E, the mating connectors 940a and 943a are shown disconnected. As shown, each connector 940a and 943a includes supply and return lines. One or both of the connectors (e.g., connector 940a) may include a valve 946 (e.g., multiple flaps of material that are configured to normally abut each other to provide a seal, but that can be opened or spread to permit coupling with and sealing against another member—as depicted in FIG. 9F, in which the connectors 940a and 943a are shown coupled). With such a valve 946, any liquid in the supply line 931a or return line 937a may be retained therein when the connectors 904a and 943a are decoupled, thereby preventing or minimizing leakage of any warming/inflating fluid onto the wearer or the wearer's clothing. A connecting mechanism, such as a clip 949 may be included on the connectors 940a to 943a to enable them to be releasably but securely coupled.

Figure 9G:
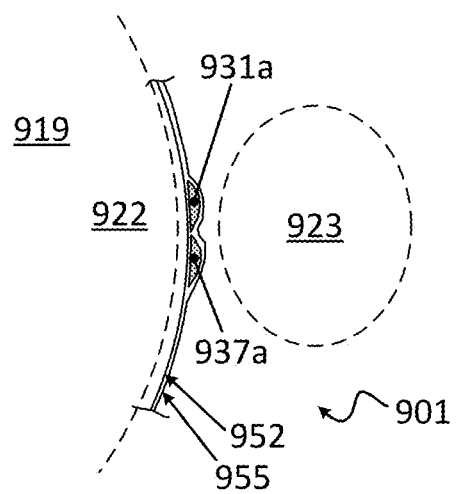
FIG. 9G is a cross-sectional view showing exemplary disposition of supply and return lines.

In some implementations, as shown in FIGS. 9B and 9G, the supply and return lines (e.g., supply line 931a and return line 937a) may be disposed on a side of the pumping top 901, such that they run between the torso 922 and arm 923 of the wearer 919. Such implementations may facilitate concealing of the lines 931a and 937a under other clothing of the wearer 919. Moreover, as shown, the lines 931a and 937a may have a flat (e.g., elongated, with a width dimension being greater than a height dimensioned) or contoured cross-section (e.g., curved, to follow a curved surface of the side of a wearer 919), to minimize discomfort associated with the lines 931a and 937a otherwise digging into the skin of the wearer 919. To further enhance comfort of the wearer, the lines 931a and 937a may be disposed between two layers of material of the pumping top 901 (e.g., between an inner layer 952 and an outer layer 955).

As shown, the lines 931a and 937a are separate lines; but in some implementations, they may be concentrically disposed, one inside of the other. Various shapes and configurations of the lines 931a and 937a are possible.

Figures 10A, 10B, 10C:
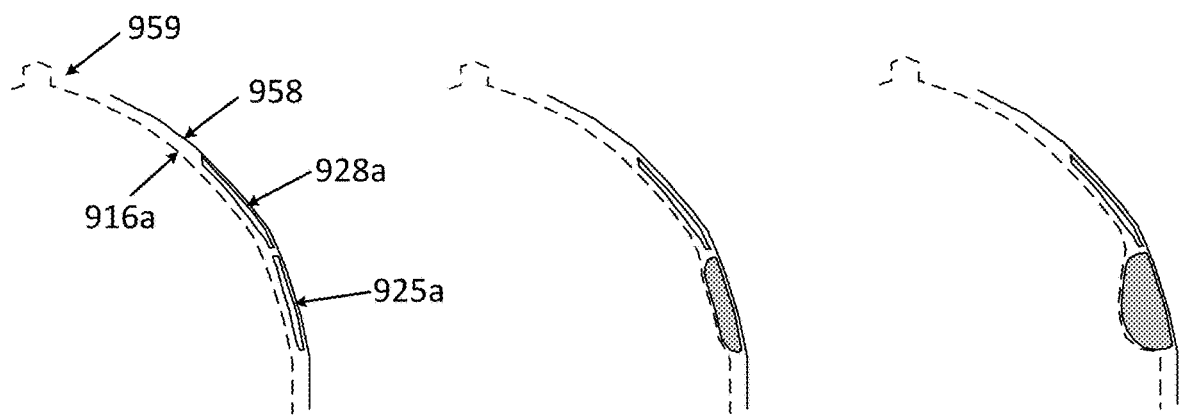
FIGS. 10A-10F depict operation of exemplary expandable bladders.
Figures 10D, 10E, 10F:
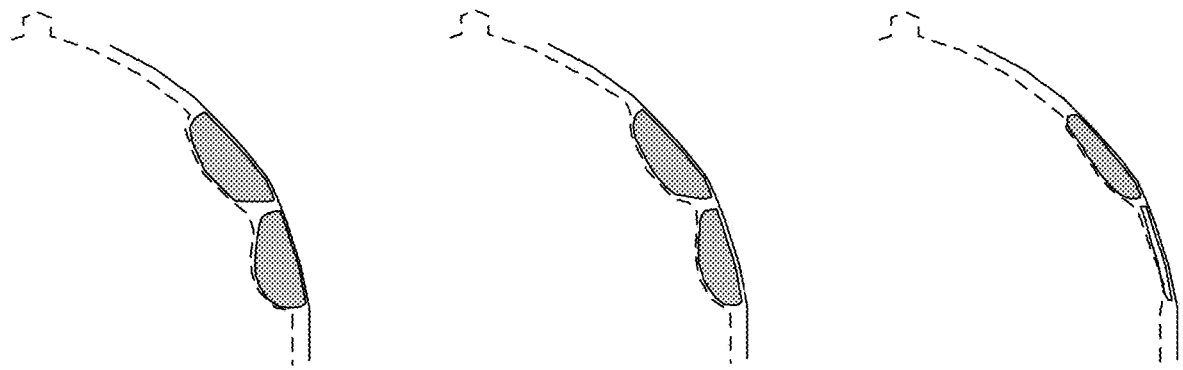

FIGS. 10A-10F depict operation of exemplary expandable bladders 925a and 928a. FIGS. 10A-10F are cross-sectional top views, showing material 958 of the pumping top 901 disposed against a breast 916a of the wearer. Expandable bladder 925a is shown in contact with a base portion of the breast 916a, and expandable bladder 928a is shown disposed against a more distal portion of the breast 916a (closer to nipple 959). Initially, both bladders 925a and 928a are empty (FIG. 10A). As the circulating pump 934 is actuated, fluid fills the expandable bladder 925a, causing it to expand and impinge on the breast 916a (FIGS. 10B-10C); fluid then travels into the expandable bladder 928a, such that both bladders 925a and 928a contain fluid (FIGS. 10C-10D); next, the circulating pump 934 begins evacuating the bladders 925a and 928a, such that bladder 925a empties, followed by bladder 928a (FIGS. 10E-10F). The circulating pump 934 may cause this cycle to be repeated, thereby effectuating a massaging motion from base of the breast 916a towards the nipple 959. In some implementations, particularly when the fluid is warmed by the circulating pump 934, milk expression may be enhanced.

In some implementations, different portions of the expandable bladders 925a and 928a may comprise different materials or have different material properties. For example, portions of bladders 925a and 928a that contact the material 958 of the pumping top 901 may be flexible but may not stretch, whereas portions of the bladders 925a and 928a that are in contact with the breast 916a may be flexible-allowing most of the distension of the bladders to be in the direction of the breast 916a, thereby focusing the massaging force there.

In some implementations, distension of the expandable bladders may be limited by the material of the bladders. For example, the bladders 925a and 928a may be configured to only inflate so far (e.g., with fibers, bands or other means to limit their distension), for safety reasons (e.g., to avoid too much pressure on the breast 916a) or to maintain the integrity of the pumping top 901 (e.g., to prevent bursting of the expandable bladders 925a and 928a).

In some implementations, the expandable bladders 925a and 928a and the supply and return lines 931a and 937a may comprise a resilient material that is configured to collapse when not subjected to pressurized fluid. Such implementations may cause fluid to be squeezed out of the expandable bladders 925a and 928a and the supply and return lines 931a and 937a when the circulating pump 934 is not actively forcing fluid therethrough-which may have the benefit of increasing comfort of the wearer when the circulating pump 934 is not in use and of minimizing any leakage when the circulating pump 934 is disconnected.

FIGS. 11A-11F depict operation of exemplary first bladder 1151 and second bladder 1152 that are arranged in a "blind channel" manner. That is, the first bladder 1151 and second bladder 1152 are arranged in series but are supplied by a single inlet/outlet 1154 at one end, through which fluid both enters and exits. As shown, a flow restrictor 1163 couples the first bladder 1151 to the second bladder 1152. A pressure gauge 1157 is shown to depict pressure on the fluid 1160 exerted by a pump (not shown) in the system (e.g., the pump 116 of FIG. 1 or the circulating pump 934 of FIG. 9B).

As depicted in FIGS. 11A-11F, each bladder 1151 and 1152 is elastic and resilient. That is, each is configured to elastically deform outward in response to pressurized fluid from within, then resiliently return to its initial state when its elastic deformation force exceeds the force that the fluid exerts on its inner surface.

Figure 11A:
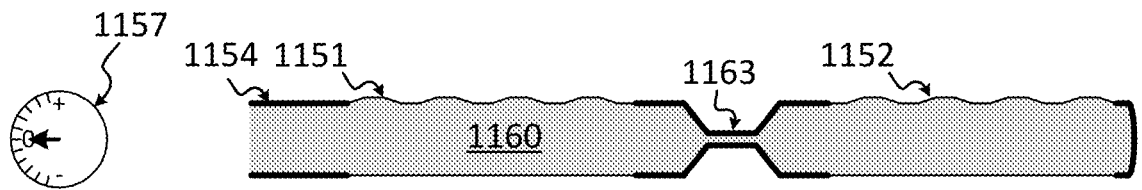
FIGS. 11A-11F depict operation of an exemplary system having first and second bladders with a flow restrictor therebetween.

FIG. 11A depicts an initial equilibrium state in which each bladder 1151 and 1152 is filled with fluid 1160, but the net pressure between that of the fluid exerted on the bladders 1151 and 1152 and that of the bladders 1151 and 1152 on the fluid is substantially zero.

Figure 11B:
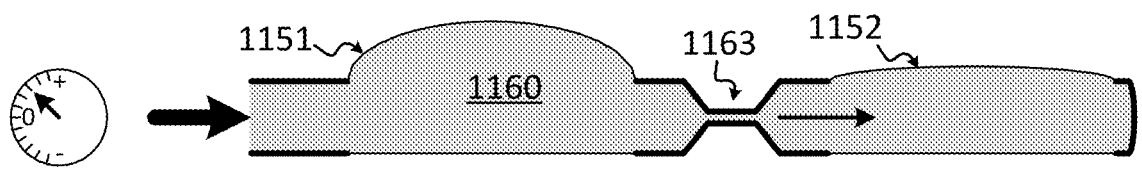

FIG. 11B depicts an increase in pressure of the fluid 1160 on the bladders 1151 and 1152 (e.g., as would occur when a pump in the system begins pumping fluid 1160 into the bladders 1151 and 1152). Because of the flow restrictor 1163, the first bladder 1151 fills (and expands) before (or to a greater extent than) the filling and expansion of the second bladder 1152, although, as depicted, some fluid 1160 begins flowing through the flow restrictor 1163, into the second bladder 1152, as the first bladder 1151 fills and expands.

Figure 11C:
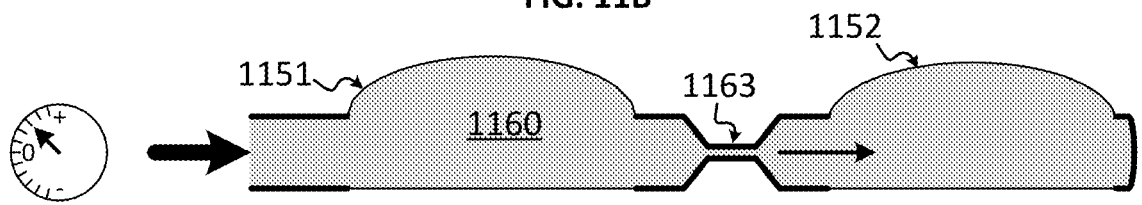
Figure 11D:
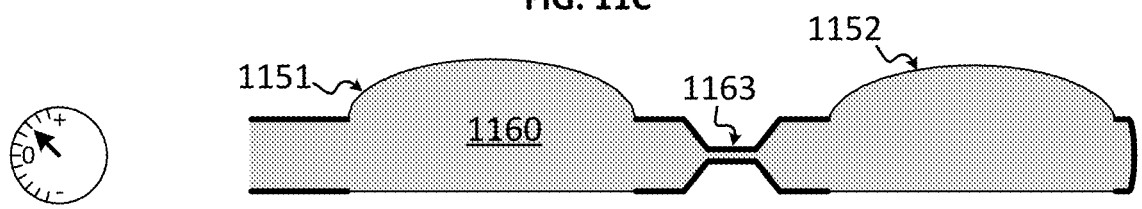

FIG. 11C depicts continued pressurized flow of fluid 1160 into the first bladder 1151 and second bladder 1152. The first bladder may reach a maximum capacity, after which further expansion or inflation may be prevented (e.g., see FIGS. 16A-16C, FIGS. 17A-17C and corresponding description). At this point, all additional fluid 1160 may flow through the first bladder 1151 and flow restrictor 1163, into the second bladder 1152, until the second bladder 1152 also reaches its maximum capacity. At this point, no more fluid 1160 may flow into the bladders 1151 and 1152, but the fluid 1160 therein may be retained in place by pressure exerted on the fluid 1160 by the pump (as depicted in FIG. 11D).

Figure 11E:
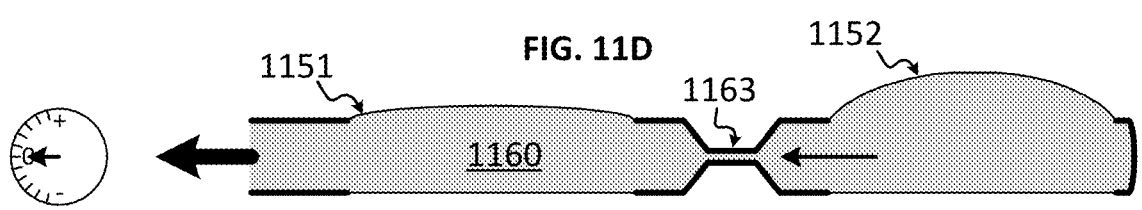

FIG. 11E depicts a release of pressure exerted on the fluid 1160 by a pump, such that the fluid 1160 is pushed out by the elastic force of the bladders 1151 and 1152. As depicted, the flow restrictor 1163 may limit the rate of outflow from the second bladder 1152, resulting in the first bladder 1151 deflating prior to the second bladder 1152.

Figure 11F:
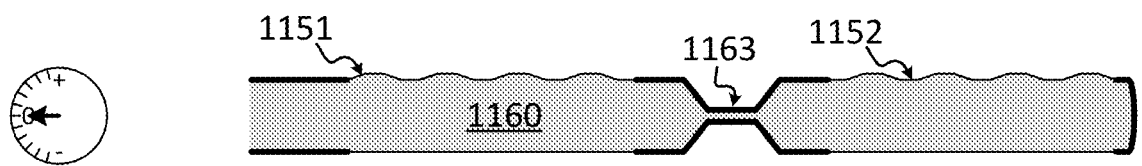

FIG. 11F depicts a return to an equilibrium state, in which the pressure of the fluid 1160 exerted on the bladders 1151 and 1152 and the elastic deformation force exerted by the bladders 1151 and 1152 on the fluid 1160 substantially balances, and the fluid 1160 present in the bladders 1151 and 1152 remains there. In some implementations, substantially all fluid 1160 present in the bladders 1151 and 1152 may be optionally evacuated (e.g., at the end of a pumping session, in order to reduce weight or bulk of the system).

In some implementations, elasticity of the first bladder 1151 and second bladder 1152 may be the same; in other implementations, elasticity of the first bladder 1151 and second bladder 1152 may be different-such that the inflation and deflation rates are affected (e.g., a less elastic, stiffer, bladder may inflate more slowly and deflate more quickly than a more elastic, less stiff bladder). Moreover, characteristics (e.g., diameter) of the flow restrictor 1163 and/or characteristics of the inlet/outlet 1154 may be "tuned" to control inflation and deflation rates of the bladders 1151 and 1152, and the relative inflation and deflation rates of the first bladder 1151 and the second bladder 1152. By changing such design constraints—the elasticity of the first bladder 1151 and second bladder 1152 and the characteristics of the inlet/outlet 1154 and the flow restrictor 1163—massage sensations produced by the sequential inflation and deflation of the bladders 1151 and 1152 may be controlled. Pump characteristics (e.g., pressure generated, flow capacity, frequency of pressure change) may also be controlled to tailor the resulting massage sensations in a desired manner.

As depicted in FIGS. 11A-11F, a pump only exerts a positive pressure on the fluid 1160 to inflate the bladders 1151 and 1152; and the bladders 1151 and 1152 then deflate when the pump stops exerting that pressure on the fluid 1160 and the force of elastic deformation of the bladders 1151 and 1152 pushes fluid 1160 out the inlet/outlet 1154. In other implementations, the pump may also exert a negative pressure on the fluid 1160 during the deflation stage, to evacuate the fluid 1160 out of the bladders 1151 and 1152 at a faster rate than is possible in the absence of such negative pressure.

FIGS. 12A-12F depict operation of an exemplary system with a first bladder 1251 and a second bladder 1252 that is also arranged in a "blind channel" manner, but that includes a one-way check valve 1264, in addition to a flow restrictor 1263 that couples the first bladder 1251 to the second bladder 1252. A pressure gauge 1257 is again shown to depict pressure on the fluid exerted by a pump in the system (not shown).

Figure 12A:
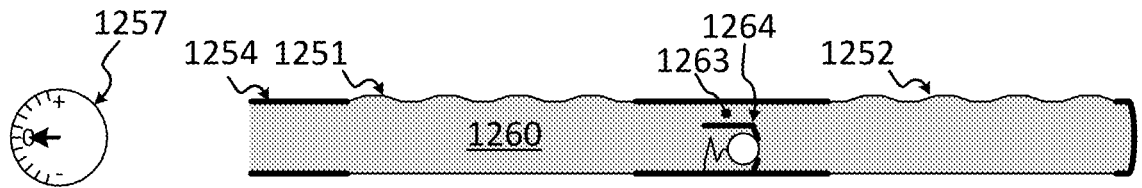
FIGS. 12A-12F depict operation of another exemplary system having first and second bladders with a flow restrictor therebetween and a check valve.

FIG. 12A depicts an initial equilibrium state in which each bladder 1251 and 1252 is filled with fluid 1260, but the net pressure between that of the fluid exerted on the bladders 1251 and 1252 and that of the bladders 1251 and 1252 on the fluid is substantially zero.

Figure 12B:
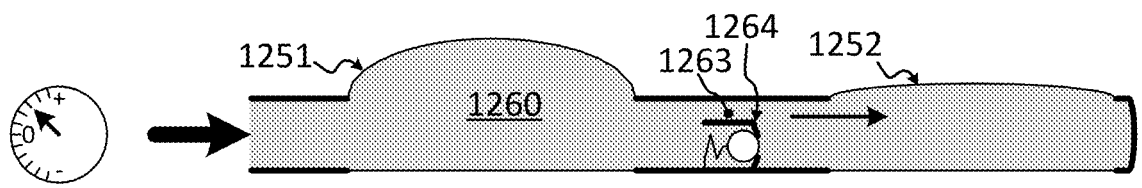

FIG. 12B depicts an increase in pressure of the fluid 1260 on the bladders 1251 and 1252 (e.g., as would occur when a pump in the system begins pumping fluid 1260 into the bladders 1251 and 1252). Because of the flow restrictor 1263 and the orientation of the check valve 1264 (opening to flow from the second bladder 1252 to the first bladder 1251, but not to flow from the first bladder 1251 to the second bladder 1252), the first bladder 1251 fills (and expands) before (or to a greater extent than) the filling and expansion of the second bladder 1252, although, as depicted, some fluid 1160 begins flowing through the flow restrictor 1263, into the second bladder 1252 as the first bladder 1251 fills and expands.

Figure 12C:
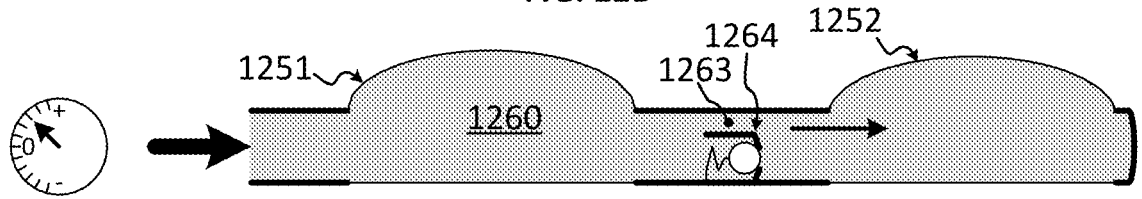
Figure 12D:
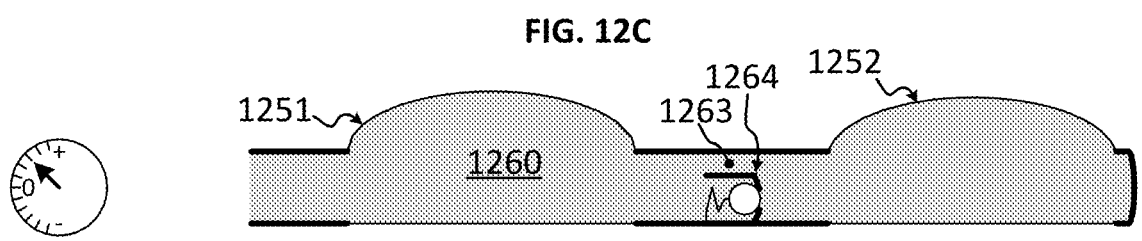

FIG. 12C depicts continued pressurized flow of fluid 1260 into the first bladder 1251 and second bladder 1252. As with the implementation depicted in FIGS. 11A-11F, the first bladder 1251 may reach a maximum capacity, after which further expansion or inflation may be prevented. At this point, all additional fluid 1260 may flow through the first bladder 1251 and flow restrictor 1263, into the second bladder 1252, until the second bladder 1252 also reaches its maximum capacity. At this point, no more fluid 1260 may flow into the bladders 1251 and 1252, but the fluid 1260 therein may be retained in place by pressure exerted on the fluid 1260 by the pump (as depicted in FIG. 12D).

Figure 12E:
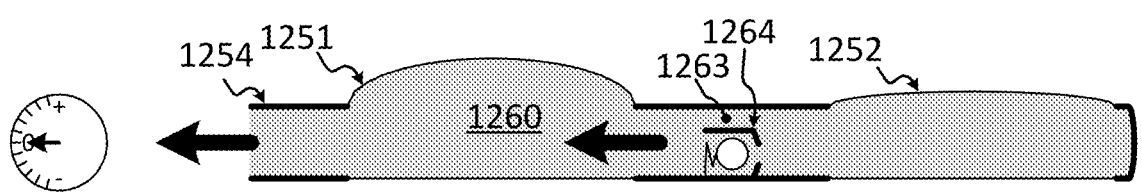

FIG. 12E depicts a release of pressure exerted on the fluid 1260 by a pump, such that the fluid 1260 is pushed out by the elastic force of the bladders 1251 and 1252. As shown, the check valve 1264 opens, allowing a larger flow from second bladder 1252 to the first bladder 1251 than was possible as fluid 1260 was flowing from first bladder 1251 to second bladder 1252. As depicted, the second bladder 1252 may deflate before the first bladder 1251, even though the combination of the flow restrictor 1263 and open check valve 1264 may facilitate a similar flow as that facilitated by the inlet/outlet 1254. In some implementations, this sequence may be facilitated by material properties of the bladders 1251 and 1252. For example, the bladder 1252 may be less elastic (stiffer) than the first bladder 1252, causing it to deflate more quickly.

Characteristics of the check valve 1263 may be adjusted, too. For example, a spring force that must be overcome to open the check valve 1263 may be weaker in a first implementation than in a second implementation, resulting in the check valve 1263 opening more in the first implementation than in the second implementation.

Figure 12F:
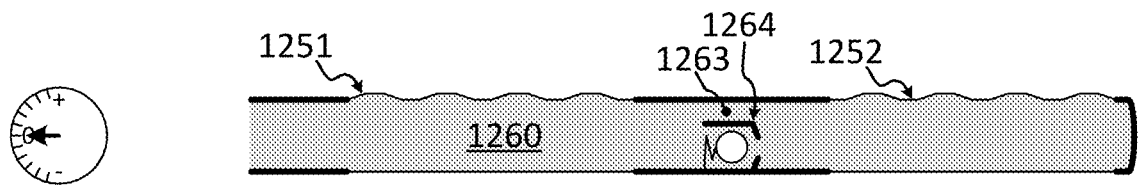

FIG. 12F depicts a return to an equilibrium state, in which relative pressure of the fluid 1260 exerted on the bladders 1251 and 1252 and elastic deformation force exerted by the bladders 1251 and 1252 on the fluid 1260 is substantially zero, and the fluid 1260 present in the bladders 1251 and 1252 remains there. In some implementations, substantially all fluid 1260 present in the bladders 1251 and 1252 may be optionally evacuated (e.g., at the end of a pumping session, in order to reduce weight or bulk of the system).

FIGS. 13A-13F depict a variation of the implementation depicted in FIGS. 12A-12F, in which fluid 1360 is pumped through an inlet/outlet 1354, into a first bladder 1351 and second bladder 1352, where a flow restrictor 1363 and check valve 1364 are disposed between the first bladder 1351 and second bladder 1352. A gauge 1357 is again provided as a reference for the pressure of the fluid 1360.

Figure 13A:
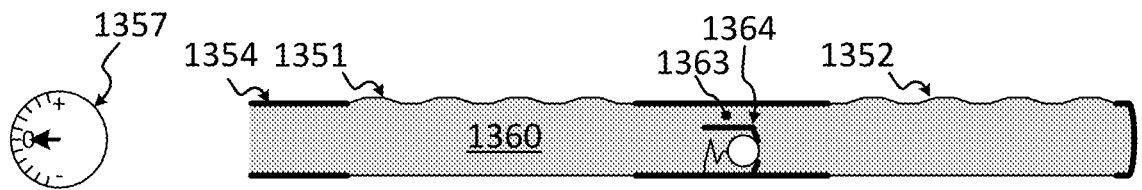
FIGS. 13A-13F depict operation of another exemplary system having first and second bladders with a flow restrictor therebetween and a check valve, wherein a negative pressure is applied to deflate the bladders.
Figure 13B:
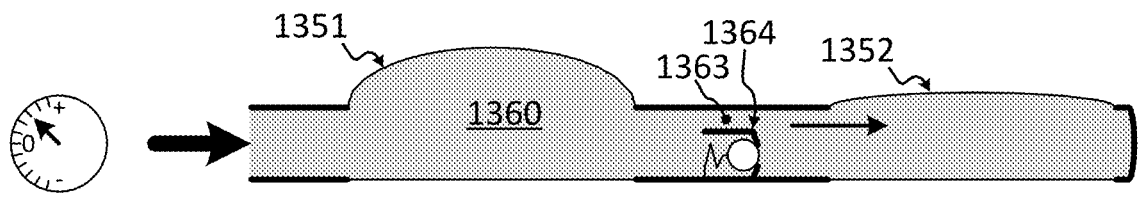
Figure 13C:
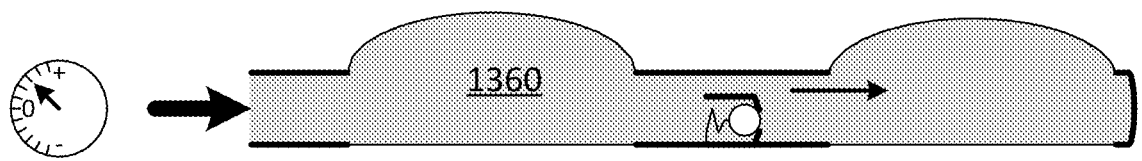
Figure 13D:
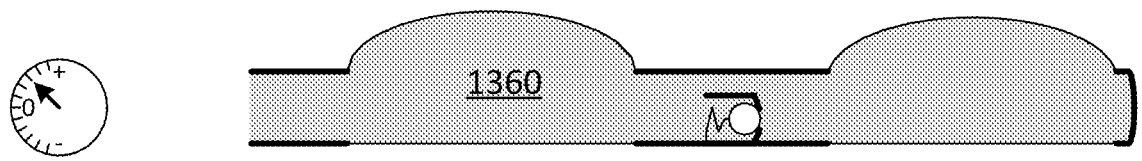

Operation of the implementation in FIGS. 13A-13F is similar to that shown in FIGS. 12A-12F: pressurized fluid 1360 inflates the first bladder 1351 faster than the second bladder 1352, in part, because of a flow restrictor 1363 and closed check valve 1364 (FIG. 13A); pressurized fluid 1360 continues to inflate the first bladder 1351 to its maximum capacity (FIG. 13B) and the second bladder 1352 to its maximum capacity (FIG. 13C); and once both bladders 1351 and 1352 are maximally inflated, continued pressure holds the fluid 1360 in place, though no fluid flows in either direction (FIG. 13D).

Figure 13E:
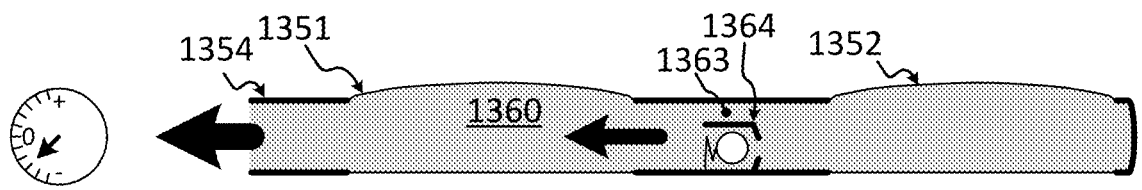

As depicted in FIG. 13E, a negative pressure may result in the bladders 1351 and 1352 deflating faster than in implementations with zero pressure—that is, a negative pressure (e.g., a pressure below atmospheric pressure) may evacuate the fluid 1360 more quickly than it would be otherwise ejected through only elastic deformation forces exerted by the bladders 1351 and 1352. As further depicted, depending on the magnitude of the pressure and the characteristics of the first bladder 1351, the second bladder 1352, the flow restrictor 1363 and the check valve 1364, it may be possible to deflate both bladders 1351 and 1352 at substantially the same time.

Figure 13F:
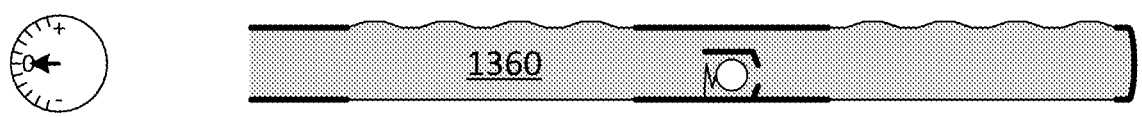

FIG. 13F depicts a return to equilibrium state, in one implementation.

FIGS. 14A-14F depict another exemplary first bladder 1451 and second bladder 1452 that are arranged in a "circulating" manner—that is, the bladders 1451 and 1452 are configured such that fluid 1460 flows into the first bladder 1451, through a dedicated inlet line 1455, and to and through the second bladder 1452, exiting through a dedicated outlet line 1456. In some implementations, the inlet line 1455 and the outlet line 1456 may be coupled at a common inlet/outlet 1454.

As shown, the first bladder 1451 is coupled to the second bladder 1452 through a flow restrictor 1463. Check valves may be provided-specifically, a first check valve 1465a that only allows fluid 1460 to move from the inlet line 1455 to the first bladder 1451, but not from the first bladder 1451 back to the inlet line 1455; and a second check valve 1465b that only allows fluid 1460 to move from the outlet line 1456 to the inlet/outlet 1454, but not from the outlet/inlet 1454 to the outlet line 1456. This implementation may provide another means for control over the sequence of deflation of the bladders 1451 and 1452—in particular, providing another manner to control deflation of the second bladder 1452 before deflation of the first bladder 1451.

Figure 14A:
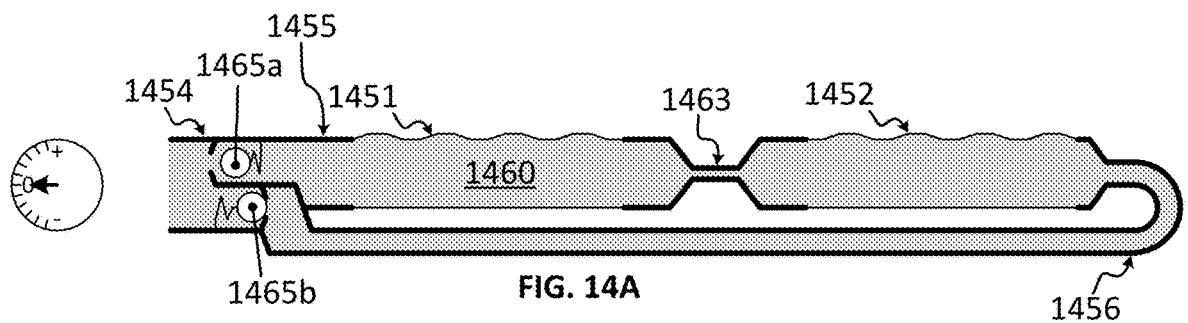
FIGS. 14A-14F depict operation of another exemplary system having first and second bladders with a flow restrictor therebetween and two check valves.
Figure 14B:
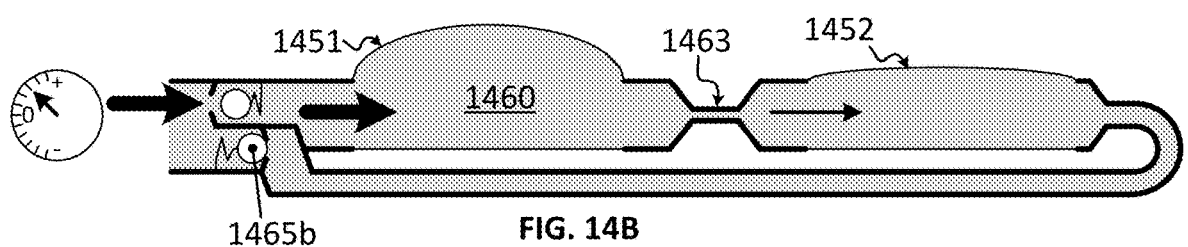
Figure 14C:
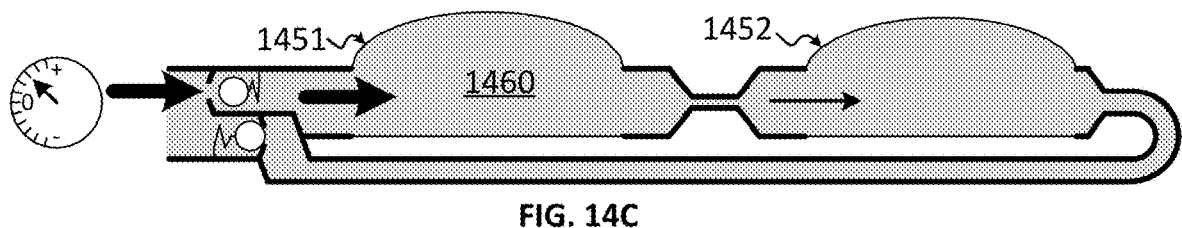
Figure 14D:
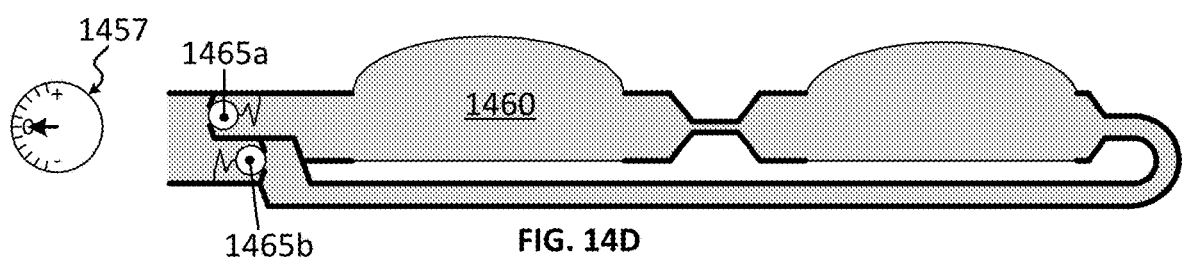

Similar to other implementations, pressurized fluid 1460 inflates the first bladder 1451 faster than the second bladder 1452, in part, because of a flow restrictor 1463 and closed check valve 1465b (FIG. 14A); and pressurized fluid 1460 continues to inflate the first bladder 1451 to its maximum capacity (FIG. 14B) and the second bladder 1452 to its maximum capacity (FIG. 14C). In some implementations, once both bladders 1451 and 1452 are maximally inflated (depending on the characteristics of the check valves 1465*a* and 1465*b* (i.e., their inherent spring force that must be overcome to cause them to open)), no additional pressure may be required (see gauge 1457, depicting zero pressure in FIG. 14D) to maintain the fluid 1460 in place.

Figure 14E:
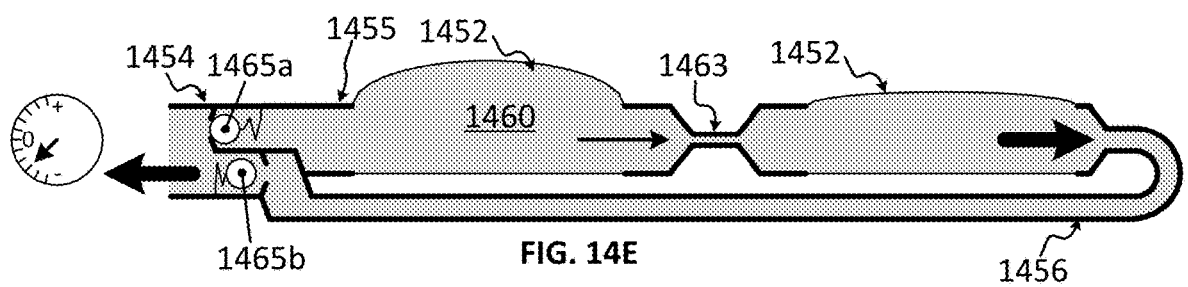

FIG. 14E depicts a negative pressure applied at the inlet/outlet 1454, which causes the fluid 1460 to be withdrawn from the bladders 1452 and 1451 through the outlet 1456 (as shown, the check valve 1465*b* opens; but the check valve 1465*a* remains closed, causing fluid 1460 to only be evacuated through the outlet line 1456). As further depicted, a diameter of the outlet line 1456 may allow for greater flow from the second bladder 1452 than that flow restrictor 1463 permits from the first bladder 1451 to the second bladder 1452—resulting in faster deflation of the second bladder 1452 than the first bladder 1451.

Figure 14F:
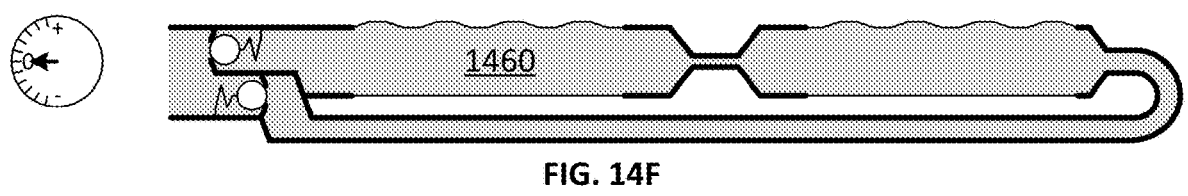

FIG. 14F depicts a return to an equilibrium state, in one implementation.

FIGS. 15A-15F depict another exemplary first bladder 1551 and second bladder 1552 that are arranged in a "circulating" manner. This implementation includes an inlet/outlet 1554, a dedicated inlet line 1555, a dedicated outlet line 1556, a flow restrictor 1563, a first check valve 1565*a* and second check valve 1565*b*. FIGS. 15A and 15F depict equilibrium states, in one implementation; FIGS. 15B and 15C depict sequential filling of the bladders 1551 and 1552 with fluid 1560; FIG. 15D depicts an equilibrium state in which the bladders 1551 and 1552 are filled to their maximum capacity. As depicted by FIG. 15E, the position of the check valve 1565*b* may facilitate substantially simultaneous deflation of the bladders 1551 and 1552.

Numerous other configurations are possible, including configurations with more bladders (three, four, five, etc.). By specifically configuring inlet lines, outlet lines, flow restrictors, elasticity of bladders, and, optionally including check valves, it may be possible to precisely stage the inflation and deflation of bladders in a manner that facilitates an effective massage function. By employing a warmed liquid as the working fluid for inflating bladders, a heating function may be combined with a massage function. Moreover, a pump for circulating fluid through the bladders and various inlet/outlet line or inlet and outlet lines, may be adjusted to provide alternating positive and zero or positive, zero and negative pressure to circulate fluid and inflate and deflate bladders in a cyclic manner. In some implementations, such inflating and deflating bladders may be used in combination with various pumping tops or garments to enhance milk production during a pumping operation by mimicking, at least in part, the massage and heat that a nursing infant may otherwise provide.

Figure 16A:
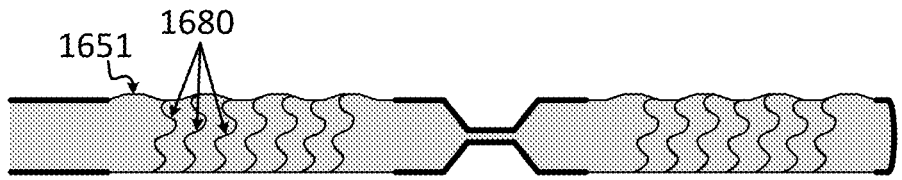
FIGS. 16A-16C illustrate one implementation in which bladders are prevented from overinflating.
Figure 16B:
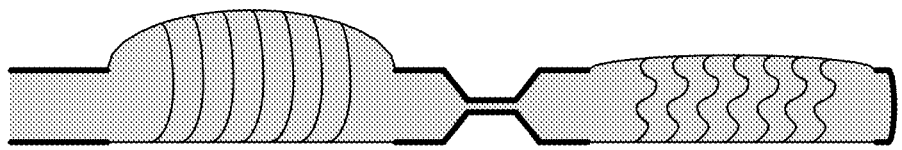
Figure 16C:
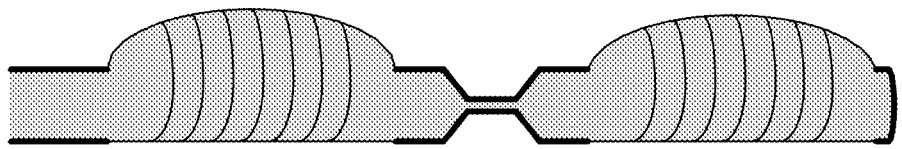

FIGS. 16A-16C illustrate one manner in which a maximum capacity, or distension, of a bladder may be limited. As shown, an outer surface of a bladder 1651 may include fibers 1680 (e.g., non-elastic fibers) that are anchored at only certain points. In a deflated state, the fibers 1680 may have some amount of slack, which may be taken up as the bladder is inflated (as depicted in FIGS. 16B and 16C). At this point, the fibers 1680 may prevent further inflation of the bladder 1651—in some implementations, preventing its rupture.

Figure 17A:
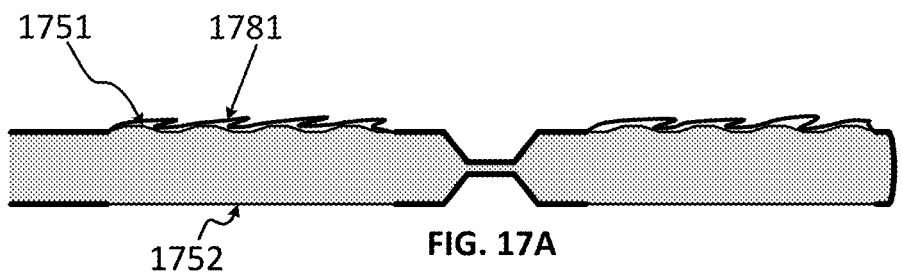
FIGS. 17A-17C illustrate another implementation in which bladders are prevented from overinflating.
Figure 17B:
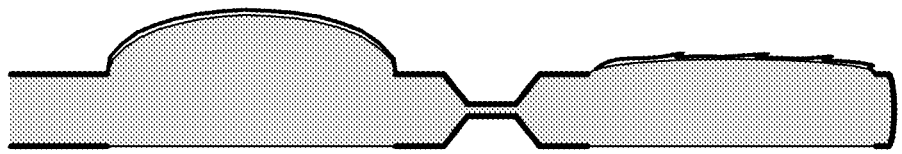
Figure 17C:
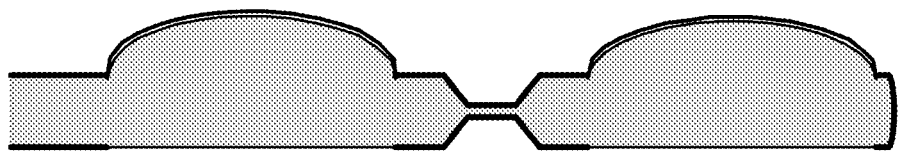

FIGS. 17A-17C illustrate another manner in which a maximum capacity, or distension, of a bladder may be limited. As shown, an elastic bladder 1751 may be covered by an inelastic material 1781. When the bladder 1751 is deflated, the inelastic material 1781 may be loose and folded or pleated (FIG. 17A), such that when the bladder is inflated (FIGS. 17B and 17C), the inelastic material 1781 stretches out to its maximum distension-thereby limiting, in some implementations, the distension of the bladder 1751 and preventing its rupture. (In FIGS. 17B and 17C, a gap between the bladder 1751 and inelastic material 1781 is exaggerated; but the reader will appreciate that, in practice, no such gap may exist.) In some implementations, another inelastic or noncompliant material 1752 may be disposed on an opposite side as the bladder 1751, such that the bladder only "inflates" in one direction (e.g., against a user's breast, rather than outward relative to the user).

Figure 18A:
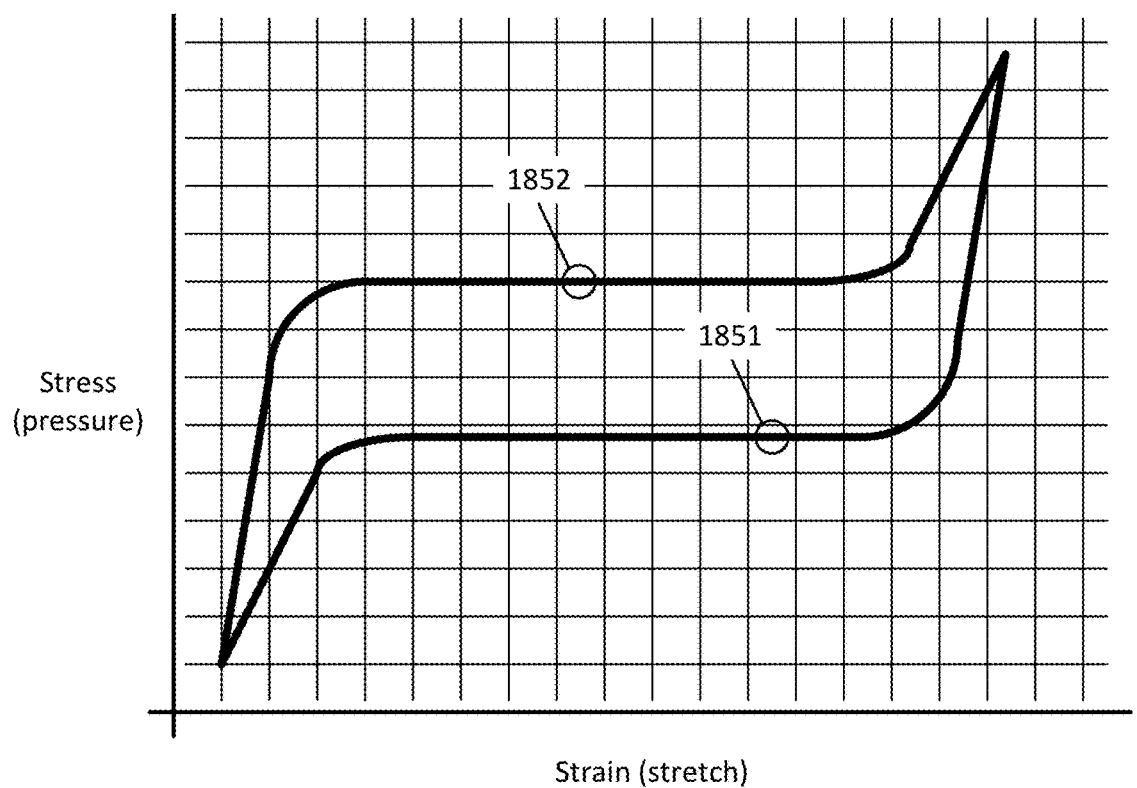
FIG. 18A illustrates an exemplary stress-strain curve that depicts the staged inflation of first and second bladders at different pressures.

FIG. 18A illustrates an exemplary stress-strain curve, in some implementations. Specifically, FIG. 18A depicts how, as pressure increases (y-axis), a first bladder 1851 may stretch (inflate); and as pressure continues to increase, a second bladder 1851 may stretch (inflate). FIG. 18A depicts an implementation in which a first bladder 1851 inflates at a first pressure, and a second bladder 1852 only inflates at a second, higher pressure.

Figure 18B:
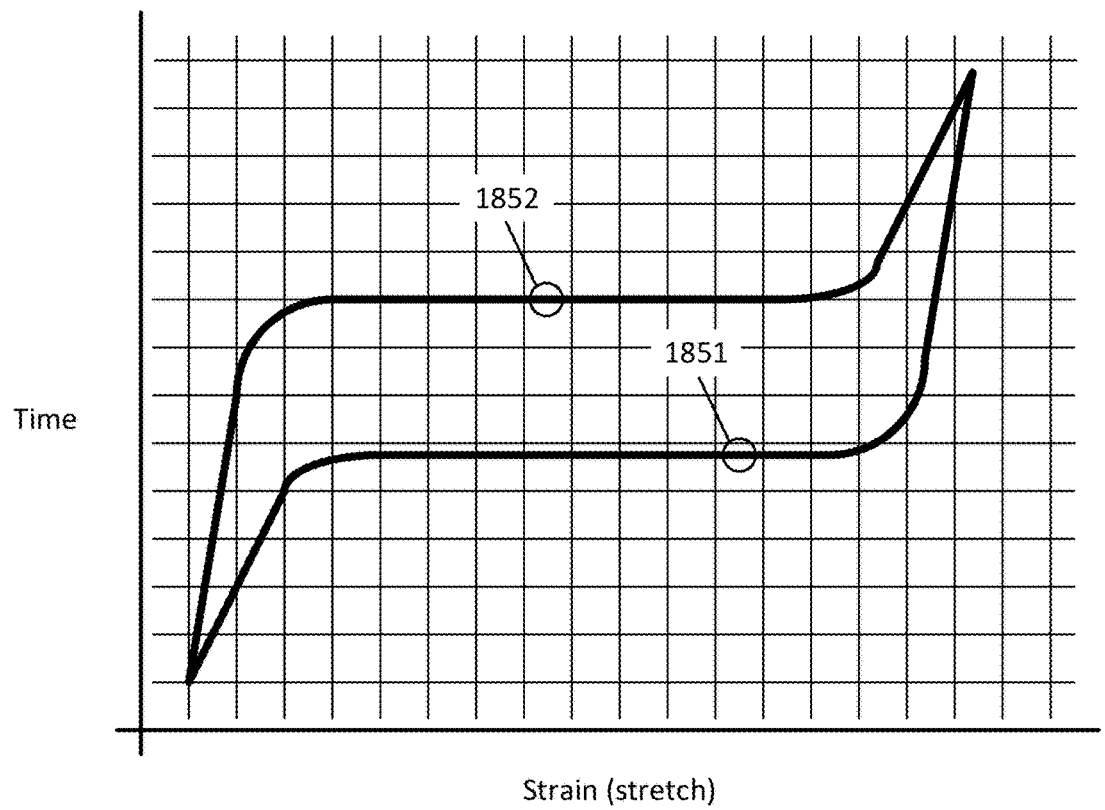
FIG. 18B illustrates an exemplary time-strain curve that depicts the staged inflation of first and second bladders at different times.

In other implementations, as depicted in FIG. 18B, both bladders 1851 and 1852 may inflate at the same pressure, but the time of inflation may be staggered. That is, at a given minimum pressure (or greater), a first bladder 1851 may first begin inflating, followed (after a short period of time) by a second bladder 1852. Specific time between inflation of the first bladder 1851 and the second bladder 1852 may depend on various factors, including, for example, any flow restrictors between the bladders 1851 and 1852, elasticity of the first and second bladders 1851 and 1852 or relative elasticity of one bladder to the other. As outlined elsewhere, various such factors may be "tuned" to sequence inflation or deflation in a desirable manner.

Several implementations have been described with reference to exemplary aspects, but it will be understood by those skilled in the art that various changes may be made and equivalents may be substituted for elements thereof without departing from the contemplated scope. For example, materials with various characteristics such as elasticity, resilience and maximum distension may be employed for bladders; "inelastic" materials may have some elasticity, but far less so than "elastic" materials; maximum capacity of bladders may be limited by the bladder material itself or by external limiting factors (e.g., fibers, inelastic covering layers); one or more check valves may be employed and at different positions; one or more flow restrictors may be employed; either "blind channel" or "circulating" implementations may be employed; various parameters may be tuned such that bladders inflate in a staged manner and deflate in various staged or substantially simultaneous manners; multiple pumps may be employed (e.g., dedicated pumps for each side, or dedicated pumps for inflating bladders and for circulating warming or cooling fluid); other variations are possible.

In some places, the term "substantially" may mean "completely" or "nearly completely." For example, the disclosure includes, "In some implementations, the first and second outer expandable elements 300*a*, 300*b* are configured to fill substantially simultaneously." In this context, "substantially" is used to mean that the first and second outer expandable elements may be configured to fill simultaneously, or there may be a slight (e.g., a few seconds) delay. For example, the first outer expandable element may begin to fill a few seconds before the second outer expandable element begins to fill (or vice-versa). This slight delay falls under the scope of "substantially simultaneously" as used in this disclosure. In other places, "substantially" (or "about"

or "approximately" may mean within 1%, or 5%, or 10%, or 20%, or 50%, or 100% of a nominal value.

Many other variations are possible, and modifications may be made to adapt a particular situation or material to the teachings provided herein without departing from the essential scope thereof. Therefore, it is intended that the scope include all aspects falling within the scope of the appended claims.

What is claimed is:

1. A pumping top comprising:
a left panel and a right panel, each of the left panel and the right panel being configured to cover a corresponding portion of a side of a wearer's torso and cover and support a corresponding breast of the wearer;
wherein each of the left panel and the right panel comprises: (i) a non-expandable reservoir that is configured to contact the corresponding breast of the wearer over substantially 360 degrees adjacent a nipple, the non-expandable reservoir further comprising an aperture which is adapted to facilitate access to the nipple for an external breast pump that is separate and distinct from the pumping top, (ii) an expandable bladder that is separate and distinct from the non-expandable reservoir, configured to be disposed more distally from the nipple than the non-expandable reservoir, fluidly coupled to the non-expandable reservoir and configured to contact and partially surround a corresponding breast of the wearer, and (iii) a line fluidly coupled at one end to one of the expandable bladder or the non-expandable reservoir and at an opposite end to a connector;
wherein the connector is configured to couple to a pump that is separate and distinct from the pumping top, which pump alternately pumps warmed liquid into the line and evacuates the liquid from the line.

2. The pumping top of claim 1, wherein each of the right and left panels comprises inner and outer layers, with the line disposed therebetween.

3. The pumping top of claim 1, wherein each connector further comprises a valve to seal off the line when it is not coupled to the pump.

4. The pumping top of claim 1, wherein the cross-sectional shape of the line is flat, with a width dimension being greater than a height dimension.

5. The pumping top of claim 1, wherein the expandable bladder of each side comprises a first expandable bladder and a second expandable bladder, wherein the first expandable bladder is coupled to the line, the second expandable bladder is coupled to a return line, and the first expandable bladder is coupled to the second expandable bladder with a tube.

6. The pumping top of claim 5, wherein the tube is non-expandable.

7. The pumping top of claim 6, wherein the tube has a reduced diameter relative to the first expandable bladder and the second expandable bladder, such that fluid flow from the first expandable bladder to the second expandable bladder is slowed to cause the first expandable bladder to fill prior to the filling of the second expandable bladder.

8. A pumping top comprising:
a left panel and a right panel, each of the left panel and the right panel being configured to cover a corresponding portion of a side of a wearer's torso and cover and support a corresponding breast of the wearer;
wherein each of the left panel and the right panel comprises a first expandable bladder and a second expandable bladder, each of the first expandable bladder and the second expandable bladder configured to contact and partially surround the corresponding breast of the wearer and each of the first expandable bladder and the second expandable bladder being fluidly coupled to separate ends of a non-expandable reservoir that is configured to contact the corresponding breast over substantially 360 degrees adjacent a nipple, and a liquid line fluidly coupled at one end to the first expandable bladder and at an opposite end to a connector;
wherein each of the left panel and the right panel has an aperture configured to receive an external breast pump that is separate and distinct from the pumping top; and
wherein the connector is configured to couple to a circulating pump that is separate and distinct from the pumping top, which circulating pump circulates warmed liquid to and from each liquid line and to and from each non-expandable reservoir.

9. The pumping top of claim 8, wherein the second expandable bladder is coupled to the first expandable bladder with a tube that includes a check valve.

10. The pumping top of claim 9, wherein the tube defines a first channel that includes the check valve and a second channel that is open between the first expandable bladder and the second expandable bladder.

11. The pumping top of claim 8, wherein the second expandable bladder is coupled to the first expandable bladder with a tube that comprises a flow restrictor that constricts flow between the first expandable bladder and the second expandable bladder.

12. The pumping top of claim 11, further comprising a return line that couples the second expandable bladder at an end opposite the tube to the liquid line.

13. The pumping top of claim 12, further comprising a check valve in the return line, in the tube, or in the second expandable bladder.

14. The pumping top of claim 13, wherein an inlet line is disposed between the liquid line and the first expandable bladder, and an inlet check valve is disposed in the inlet line.

15. The pumping top of claim 13, further comprising a second check valve in the return line.

16. The pumping top of claim 8, wherein each of the first expandable bladder and the second expandable bladder comprises means for limiting its distension.

17. The pumping top of claim 8, wherein each of the first expandable bladder and the second expandable bladder comprises non-elastic fibers that are configured to limit distension of the first expandable bladder and the second expandable bladder.

* * * * *